United States Patent [19]

Torley et al.

[11] Patent Number: 4,876,252

[45] Date of Patent: Oct. 24, 1989

[54] 4,5,6-SUBSTITUTED-N-(SUBSTITUTED-PHENYL)-2-PYRIMIDINAMINES

[75] Inventors: Lawrence W. Torley, Washingtonville; Bernard D. Johnson, Stony Point; John P. Dusza, Nanuet, all of N.Y.

[73] Assignee: American Cyanamid Company, Wayne, N.J.

[21] Appl. No.: 194,751

[22] Filed: May 17, 1988

Related U.S. Application Data

[60] Division of Ser. No. 927,572, Nov. 6, 1986, Pat. No. 4,788,195, which is a continuation-in-part of Ser. No. 817,951, Jan. 13, 1986, abandoned.

[51] Int. Cl.$^4$ ............................................. A61K 31/505
[52] U.S. Cl. ................. 514/224.8; 514/235.8; 514/252; 514/253; 514/254; 514/275; 544/35; 544/122; 544/330; 544/331; 544/332
[58] Field of Search ................. 514/224.8, 235.8, 252, 514/253, 254, 275

[56] References Cited

U.S. PATENT DOCUMENTS

| | | | |
|---|---|---|---|
| 3,980,781 | 9/1976 | Snell et al. | 544/295 |
| 4,263,300 | 4/1981 | Stähle et al. | 544/331 |
| 4,512,993 | 4/1985 | Lesher et al. | 544/331 |

OTHER PUBLICATIONS

Hashimoto et al., "Chemical Abstracts", vol. 104, 1986, col. 104:186441p.

*Primary Examiner*—Glennon H. Hollrah
*Assistant Examiner*—James H. Turnipseed
*Attorney, Agent, or Firm*—Kenneth J. Dow; Edward A. Conroy, Jr.

[57] ABSTRACT

This disclosure describes novel 4,5,6-substituted-N-(substituted-phenyl)-2-pyrimidinamines having anti-asthmatic activity.

1 Claim, No Drawings

4,5,6-SUBSTITUTED-N-(SUBSTITUTED-PHENYL)-2-PYRIMIDINAMINES

CROSS REFERENCE TO RELATED APPLICATION

This application is a division of our copending application Ser. No. 927,572, filed Nov. 6, 1986, now U.S. Pat. No. 4,788,195, which is a continuation-in-part of our abandoned application Ser. No. 817,951, filed Jan. 13, 1986, abandoned.

BRIEF SUMMARY OF THE INVENTION

This invention relates to new organic compounds and, more particularly, is concerned with novel 4,5,6-substituted-N-(substituted-phenyl)-2-pyrimidinamines having anti-asthmatic activity which may be represented by the following structural formula:

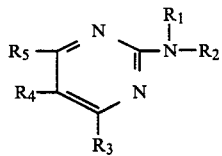

wherein $R_1$ is hydrogen, alkyl($C_1$-$C_3$), —$COCO_2C_2H_5$ or N,N-dimethylaminoethyl; $R_2$ is mono- or poly-substituted phenyl wherein the substituents are alkyl(-$C_1$-$C_6$), alkoxy($C_1$-$C_3$), chloro, bromo, iodo, trifluoromethyl, hydroxy, phenyl, amino, monoalkyl-($C_1$-$C_3$-)amino, dialkyl($C_1$-$C_3$)amino, alkyl($C_1$-$C_3$)keto, propenyloxy, carboxyl, oxyacetic acid, oxyacetic acid ethyl ester, sulfamilamido, N,N-dialkyl($C_1$-$C_3$)sulfamilamido, N-methylpiperazinyl, piperidinyl, 1H-imidazol-1-yl, 1H-triazol-1-yl, 1H-benzimidazol-2-yl, 1-naphthyl, cyclopentyl, 3,4-dimethylbenzyl or moieties of the formula:

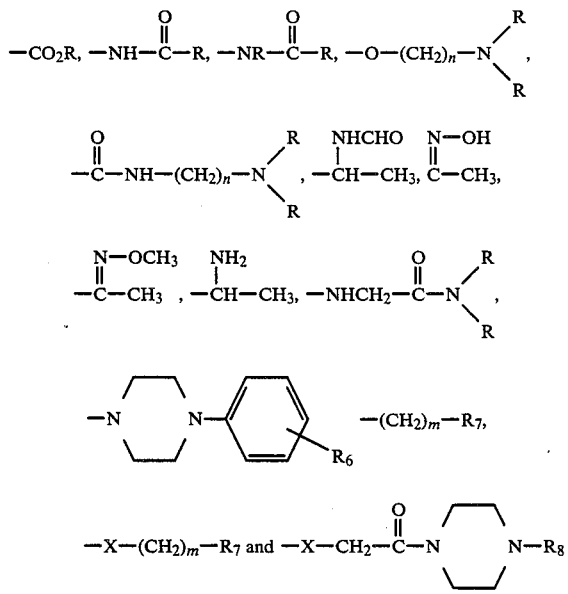

wherein R is alkyl($C_1$-$C_3$), X is oxygen (—O—) or sulfur (—S—), m is 1-3, n is 2 or 3, $R_6$ is hydrogen, alkyl($C_1$-$C_3$), alkoxy ($C_1$-$C_3$), chloro, bromo, iodo or trifluoromethyl, $R_7$ is 1H-imidazol-1-yl or morpholino and $R_8$ is alkyl($C_1$-$C_3$), phenyl or monosubstituted phenyl wherein the substituents are alkyl($C_1$-$C_3$), halogen or trifluoromethyl; $R_3$ is 2-pyridinyl, 3-pyridinyl, 4-pyridinyl, 2-methyl-3-pyridinyl, 4-methyl-3-pyridinyl, 2-furanyl, 5-methyl-2-furanyl, 2,5-dimethyl-3-furanyl, 2-thienyl, 3-thienyl, 5-methyl-2-thienyl, 2-pheno-thiazinyl, 4-pyrazinyl, 2-benzofuranyl, 2-(pyridine-N-oxide), 3-(pyridine-N-oxide), 4-(pyridine-N-oxide), 1H-indol-2-yl, 1H-indol-3-yl, 1-methyl-1H-pyrrol-2-yl, 4-quinolinyl, 4-pyridinyl methyl iodide, dimethylaminophenyl or N-acetyl-N-methylaminophenyl; $R_4$ is hydrogen or alkyl($C_1$-$C_3$); and $R_5$ is hydrogen or alkyl($C_1$-$C_3$); and the pharmacologically acceptable acid-addition salts thereof.

The present invention also includes novel compositions of matter containing the above-defined compounds which are useful for treating asthma, allergic diseases, inflammation and diabetes in mammals. The invention also comprises processes of preparing the compounds within the scope of the above formula.

DETAILED DESCRIPTION OF THE INVENTION

The novel compounds of the present invention are obtainable as crystalline materials having characteristic melting points and absorption spectra. They are in general sparingly soluble in organic solvents such as lower alkanols, chloroform, tetrahydrofuran, N,N-dimethylformamide, dichloromethane, acetone and the like, but are generally insoluble in water.

The novel 4,5,6-substituted-2-pyrimidinamines of the present invention in general may be prepared as set forth in the following reaction schemes.

Scheme I

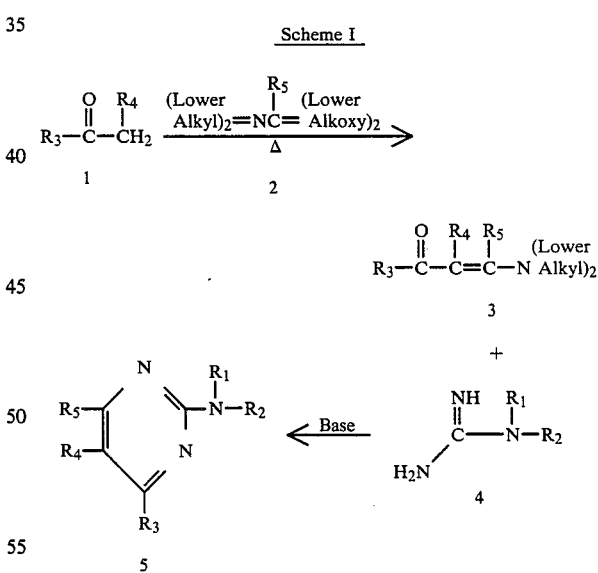

wherein $R_1$, $R_2$, $R_3$, $R_4$ and $R_5$ are as hereinabove defined.

In accordance with Scheme I, a heteroaryl ($R_3$) alkanoyl ($R_4$) compound 1, e.g 2-acetylpyridine, 2-acetylfuran, 3-acetylthiophene, 2-acetyl-6-methylpyridine, 2-propionyl pyridine or 3-propionyl pyridine and the like, is reacted with a di(lower alkyl)-formamide or acetamide di(lower alkyl) acetal 2, e.g; N,N-dimethylformamide dimethylacetal or N,N-dimethylacetamide dimethylacetal at an elevated temperature in the range of about 50° C. to about 150° C. for from about 4 to 24 hours to produce the 3di(lower alkyl)aminoacrylophenone 3. The acrylophenone 3 is then reacted with an appropriately substituted phenylguanidine ($R_1$) ($R_2$), 4 as the base or as the carbonate, sulfate, nitrate, hydrochloride or dihydrochloride salt in an inert solvent such as absolute ethanol, n-propanol, isopropyl alcohol or 2-methoxyethanol and the like, by heating at the reflux temperature for from 6-48 hours. The product 5 is separated by the partial evaporation of the solvent, then cooling and collected and recrystallized in a conventional manner from solvents such as n-propyl alcohol, isopropyl alcohol, absolute ethyl alcohol or 2-methoxyethanol and the like and combinations of solvents such as chloroform/hexane, dichoromethane/hexane or isopropyl alcohol/ethylene glycol monomethyl ether and the like.

Scheme II

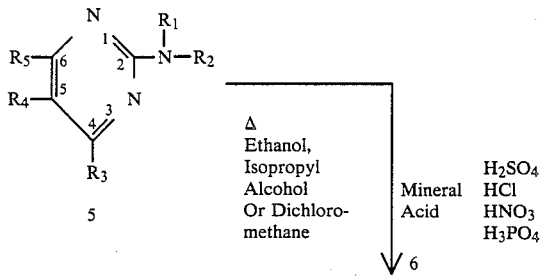

wherein $R_1$, $R_2$, $R_3$, $R_4$ and $R_5$ are as hereinabove defind.

In accordance with Scheme II, when the 4,5,6-substituted-2-pyrimidinamine product 5 is dissolved by heating in a solvent such as absolute ethanol, isopropyl alcohol or dichloromethane, then stirred at room temperature and reacted with a mineral acid such as sulfuric acid, hydrochloric acid, nitric acid or phosphoric acid and the like, dissolved in absolute ethanol or isopropyl alcohol and the like, the 4,5,6-substituted-2-pyrimidinamine acid addition salt 6 is precipitated on standing for 30 minutes and chilling for several hours.

Alternatively, acid addition salts may be formed with organic acidds such as citric acid or maleic acid and the like by dissolving the desired 4,5,6-substituted-2-pyrimidinamine in hot, absolute ethanol or 2-methoxyethanol in the presence of the organic acid. Cooling provides the desired compounds as solids.

The novel compounds of the present invention are highly active as antiasthmatic and antiallergic agents as will be demonstrated hereinbelow.

The bromochospasm of allergic asthma is a consequence of the release of mediators, such as histamine and slow-reacting substances from masts cells. The role of mediator release in the induction of an asthmatic attack has been fully reviewed and documented; see Kaliner, M. and Austen, K. F., Bronchial Asthma Mechanisms and Therepautics, E. B. Weiss, Editor, Little, Brown and Company, Boston, 163, (1976); Lichtenstein, L. M., Asthma-Physiology, Immunopharmacology and Treatment, Second International Symposium, L. M. Lichtenstein and K. F. Austen, Editors, Academic Press, New York, 51, (1979); and Bell, S. C., et al., Annular Reports in Medicinal Chemistry, 14, 51, H, J. Hess, Editor, Academic Press, New York, (1979), The novel compounds of this invention have been tested by the procedure of Lichtenstein, L. M. and Osler, A. G., J. Exp. Med., 120, 507–530 (1964), which evaluates the ability of compounds to inhibit mediator (histamine) release from immunologically stimulated human basophils.

Reagents

10X Concentrated Tris Buffer

Dissolve 140.3 g of sodium chloride, 7.45 g of Trizma-Tris Pre-Set, Reagent Grade, pH 7.6, at 25° C. (Sigma Chemical Co.) in sufficient water to give a final volume of 2 liters.

Human Albumin (Sigma Chemical Co.) (30 mg/ml)

Calcium and Magnesium Stocks

Made to 0.075M 0.5M respectively, with calcium chloride dihydrate and magnesium chloride hexahydrate.

Tris-A Buffer A 10 ml portion of 10X Tris Buffer and 1.0 ml of human albumin are diluted to 100 ml with water.

Tris ACM Buffer

A 10 ml portion of 10X Tris Buffer, 1.0 ml of human albumin, 0.8 ml of calcium stock and 0.2 ml of magnesium stock are diluted to 100 ml with water.

Rabbit Antihuman IgE

Behring Diagnostics (Generally used at 10 μg protein/ml final concentration).

House Dust Mite Extract (*Dermatophagoides Farinae*)

Strength 1:100 (w:v) allergenic extract, Hollister-Stier Labs. Generally this is diluted 1:1000 to 1:10,000 (considering the vial as stock).

Other Allergens

Interdermal solutions or intramuscular preparations for hyposensitization, Hollister-Steir Labs. The final concentration used is on the order of 1 PNU/ml.

Separation of Leukocytes from Human Blood and Challenge

Eighty milliliters of blood is withdrawn from subjects with known histamine release to anti-IgE, ragweed antigen or other specific allergen, using four 20 ml heparinized tubes. This 80 ml of blood is mixed with 20 ml of saline containing 0.6 g dextrose and 1.2 g of dextran. The blood is allowed to sediment at room temperature in two 50 ml polycarbonate centrifuge tubes until a sharp interface develops between the red cells and plasma (60–90 minutes). The plasma (top) layer from each tube is withdrawn by pipet and transferred to respective 50 ml polycarbonate tubes. The plasma is centrifuged for 8 minutes at 110X G at 4° C. The supernatant is carefully poured off as completely as possible and the cell button is resuspended in 2-3 ml of Tris-A buffer using a siliconized Pasteur pipet. The resuspension is accomplished by drawing the liquid gently in an out of the pipet, with the tip below the liquid until an even suspension of cells is obtained. Sufficient Tris-A-buffer is then added to bring the volume in the tube to about 45 ml and the tube is centifuged at 110X G for 8 minutes at 4° C. The supernatant is poured off and the cell button is resuspended and centrifuged as described above. The supernatant is poured off and the cell button is suspended in 2-3 ml of Tris-ACM buffer to make the final volume sufficient to allow addition to the reaction tubes.

Reaction tubes containing anti-IgE or antigens, either alone or with test compound in a total volume of 0.2 ml are prepared and placed in a 37° C. bath. The cells are warmed to 37° C. and frequently swirled to ensure an even suspension, while 1.0 ml aliquots are added to each reaction tube. The tubes are then incubated for 60 minutes at 37° C., vortexing the tubes gently every 15 minutes to keep the cells evenly suspended. When the reaction is complete, the tubes are centrifuged at 4° C. for 10 minutes at 1500 rpm to sediment the cells. One ml aliquots of supernatant are transferred to 12 mm by 75 mm polyethylene tubes and 0.2 ml of 8% perchloric acid is added to each tube. Blanks and totals are included in each test. The blanks have cells and all reagents except antigen or anti-IgE. The totals contain 0.24 ml of 8% perchloric acid, one ml of cells and 0.2 ml of buffer. All samples are the centrifuged to remove the precipitate protein.

Assay of Released Histamine by the Automated Fluorometric Method

This automated method has been described by Siraganian, R. P., in Anal. Biochem., 57, 383 (1974) and J. Immunol. Methods, 7, 283 (1975) and is based on the manual method of Shore, P. A., et al., J. Pharmacol. Exp. Ther., 217, 182 (1959).

The automated system consists of the following Technicon Autoanalyzer II components: Sampler IV, Dual-Speed Proportioning Pump III, Fluoronephelometer with a narrow pass primary filter 7-60 and a secondary filter 3-74, Recorder, and Digital Printer. The manifold used is the one described by Siraganian vide supra, with the following modifications: the dialyzer is omitted; all pumping tubes pass through a single proportioning pump with large capacity and twice the volume of sample is taken for analysis.

The automated chemistry consists of the following steps: Extraction from alkaline saline into butanol, back extraction into dilute hydrochloric acid by addition of heptane, reaction of histamine with o-phthaldialdehyde (OPT) at high pH and conversion of the OPT adduct to a stable fluorophore with phosphoric acid. The reaction product is then passed through the fluorometer. The full scale response is adjusted to 50 ng histamine base with a threshold sensitivity of approximately 0.5 ng.

Calculation of the Results of Histamine Release Tests

The instrument blank (wash) is substracted from the ng histamine of each sample. Then the ng histamine of each sample is divided by the mean of the three totals (cells lysed with perchloric acid) to obtain percent release.

Control samples contain antigen but no test compound. Blank (or spontaneous release) samples contain neither antigen nor test compound. The means of the blanks (three replicates) is subtracted from the percent release for controls and test compounds.

The means for control and test compound groups are computed and the result for a test compound is computed as percent of control by the formula:

$$100 \times \frac{\% \text{ Histamine Release with Test Compound}}{\% \text{ Histamine Release in Controls}}$$

Values obtained at different concentrations of test compound are used to calculate an $IC_{50}$ (the concentration in $\mu M$ which causes a 50% inhibition of histamine release) by linear regression. A compound is considered active if the $IC_{50}$ is $\geq 48$ $\mu M$.

The results of this test on typical compounds of this invention appear in Table I.

TABLE I

| Inhibition of Histamine Release from Immunologically Stimulated Human Basophils | |
|---|---|
| Compound | $IC_{50}(\mu M)$ |
| 4-(2-Furanyl)-5-methyl-N—phenyl-2-pyrimidinamine | 17.7 |
| 4-(4-Pyridinyl)-N—[(3-trifluoromethyl)phenyl]-2-pyrimidinamine | 32.0 |
| N—(4-Methoxyphenyl)-4-(3-pyridinyl)-2-pyrimidinamine | 1.4 |
| N—Phenyl-4-(3-pyridinyl)-2-pyrimidinamine | 0.9 |
| N—(4-Acetylphenyl)-4-(3-pyridinyl)-2-pyrimidinamine | 0.8 |
| N—(4-Fluorophenyl)-4-(3-pyridinyl)-2-pyrimidinamine | <48 |
| N—(4-Methoxyphenyl)-4-(2-pyridinyl)-2-pyrimidinamine | 8.3 |
| N—(4-Methoxyphenyl)-4-(4-pyridinyl)-2-pyrimidinamine | 1.0 |
| N—(4-Fluorophenyl)-4-(4-pyridinyl)-2-pyrimidinamine | 1.9 |
| N—(4-Bromophenyl)-4-(3-pyridinyl)-2-pyrimidinamine | 2.3 |
| 4-(3-Pyridinyl)-N—[3-(trifluoromethyl)phenyl]-2-pyrimidinamine, hydrochloride | 0.7 |
| 4-(2-Pyridinyl)-N—[3-(trifluoromethyl)phenyl]-2-pyrimidinamine | 2.9 |
| N—(4-Methoxyphenyl)-4-(2-thienyl)-2-pyrimidinamine | 3.9 |
| N—(4-Ethylphenyl)-4-(1-methyl-1H—pyrrol-2-yl)-2-pyrimidinamine | <48 |
| N—Phenyl-4-(2-thienyl)-2-pyrimidinamine | 31.7 |
| N—(3-Chloro-4-methylphenyl)-4-(3-pyridinyl)-2-pyrimidinamine | 9.3 |
| N—(3-Methylphenyl)-4-(2-pyridinyl)-2-pyrimidinamine | 0.7 |
| N—(3-Methylphenyl)-4-(4-pyridinyl)-2-pyrimidinamine | 9.4 |
| N—Phenyl-4-(4-pyridinyl)-2-pyrimidinamine | 0.9 |
| N—(3-Methylphenyl)-4-(3-pyridinyl)-2-pyrimidinamine | 1.5 |
| N—(4-Ethylphenyl)-4-(4-pyridinyl)-2-pyrimidinamine | 7.7 |
| N—(4-Ethylphenyl)-5-methyl-4-(4-pyridinyl)-2-pyrimidinamine | <48 |
| N—4-Ethylphenyl)-4-(3-pyridinyl)-2-pyrimidinamine | <48 |
| N—(4-Ethylphenyl)-4-(2-pyridinyl)-2-pyrimidinamine | 2.1 |
| N—(3-Methylphenyl)-4-(2-thienyl)-2-pyrimidinamine | 0.3 |
| 4-(2-Furanyl)-N—phenyl-2-pyrimidinamine | 48 |
| 4-(2-Furanyl)-N—(3-methylphenyl)-2-pyrimidinamine | 3.5 |
| N—(4-Ethylphenyl)-4-(6-methyl-3-pyridinyl)-2-pyrimidinamine | 13.4 |
| N—(4-Ethylphenyl)-6-methyl-4-(6-methyl-3-pyridinyl)-2-pyrimidinamine | 19.1 |
| N—[4-(4-Methyl-1-piperazinyl)phenyl]-4-(2-thienyl)-2-pyrimidinamine | <24 |
| N—(4-Ethylphenyl)-4-pyrazinyl-2-pyrimidinamine | 2.8 |
| N—(3-Methylphenyl)-4-pyrazinyl-2-pyrimidinamine | 5.4 |
| N—(2-Methylphenyl)-4-(4-pyridinyl)-2-pyrimidinamine | 3.9 |
| N—(3-Ethylphenyl)-4-(4-pyridinyl)-2-pyrimidinamine | 10.6 |
| N—(2,5-Dimethylphenyl)-4-(4-pyridinyl)-2-pyrimidinamine | 47.1 |
| N—(2,3-Dimethylphenyl)-4-(4-pyridinyl)-2-pyrimidinamine | 20.2 |
| N—(3-Methylphenyl)-4-(3-thienyl)-2-pyrimidinamine | 3.8 |
| N—(2,5-Dimethylphenyl)-4-(2-pyridinyl)-2-pyrimidinamine | <48 |
| N—(3,5-Dimethylphenyl)-4-(4-pyridinyl)-2- | 4.4 |

TABLE I-continued

Inhibition of Histamine Release from Immunologically Stimulated Human Basophils

| Compound | IC$_{50}$(μM) |
| --- | --- |
| pyrimidinamine | |
| N—1-Naphthalenyl-4-(4-pyridinyl)-2-pyrimidinamine | 31.3 |
| N—(3,5-Dimethylphenyl)-4-(2-pyridinyl)-2-pyrimidinamine | 1.0 |
| N—1-Naphthalenyl-4-(2-pyridinyl)-2-pyrimidinamine | 3.0 |
| N—(2,4-Dimethylphenyl)-4-(4-pyridinyl)-2-pyrimidinamine | 24.0 |
| 4-(4-Pyridinyl)-N—(2,4,6-trimethylphenyl)-2-pyrimidinamine | 10.5 |
| 4-(2-Furanyl)-N—(4-methoxyphenyl)-2-pyrimidinamine | <48 |
| N—[4-(4-Methyl-1-piperazinyl)phenyl]-4-(2-pyridinyl)-2-pyrimidinamine | <24 |
| 4-(2-Furanyl)-N—[3-(trifluoromethyl)phenyl]-2-pyrimidinamine | <48 |
| N—(4-Fluorophenyl)-4-(2-furanyl)-2-pyrimidinamine | 13.3 |
| N—Cyclopentyl-4-(2-pyridinyl)-2-pyrimidinamine | 2.2 |
| N—Phenyl-4-(4-pyridinyl)-2-pyrimidinamine, compound with 2-hydroxy-1,2,3-propanetricarboxylate (2:1) | 3.5 |
| N—Phenyl-4-(4-pyridinyl)-2-pyrimidinamine, (Z)-2-butenedioate (1:1) | 1.0 |
| N—Phenyl-4-(4-pyridinyl)-2-pyrimidinamine, sulfate | 3.0 |
| N—Phenyl-4-(4-pyridinyl)-2-pyrimidinamine, dinitrate | 1.2 |
| N—(4-Ethylphenyl)-4-(4-pyridinyl)-2-pyrimidinamine, pyridine-1-oxide | 17.7 |
| N—(3,4-Dimethylphenyl)-4-(2-pyridinyl)-2-pyrimidinamine | 5.9 |
| N—(4-Methoxyphenyl)-4-(3-thienyl)-2-pyrimidinamine | 15.6 |
| N—(3-Ethylphenyl)-4-(2-furanyl)-2-pyrimidinamine | 9.7 |
| 4-(1H—Indol-3-yl)-N—phenyl-2-pyrimidinamine | 3.0 |
| N—(2-Methoxy-5-methylphenyl)-4-(4-pyridinyl)-2-pyrimidinamine | 6.9 |
| N—(3-Methylphenyl)-4-(1-methyl-1H—pyrrol-2-yl)-2-pyrimidinamine | 9.4 |
| N—(3-Ethylphenyl)-4-(2-thienyl)-2-pyrimidinamine | 48.0 |
| N—(3-Ethylphenyl)-4-(3-thienyl)-2-pyrimidinamine | 1.1 |
| 4-(1H—Indol-2-yl)-N—(3-methylphenyl)-2-pyrimidinamine | 2.2 |
| 4-[[4-(4-Pyridinyl)-2-pyrimidinyl]amino]-benzoic acid, methyl ester | 27.5 |
| N—(3-Methylphenyl)-4-(4-quinolinyl)-2-pyrimidinamine | 10.9 |
| N—Phenyl-4-(-4-quinolinyl)-2-pyrimidinamine | 3.0 |
| N—(4-Ethylphenyl)-4-(4-quinolinyl)-2-pyrimidinamine | 4.0 |
| 4-(2-Pyridinyl)-N—[3-(trifluoromethyl)phenyl]-2-pyrimidinamine, sulfate | 3.0 |
| N—(3-Methylphenyl)-4-(2-thienyl)-2-pyrimidinamine, sulfate | 3.0 |
| 4-(2-Furanyl)-N—[3-(methylphenyl)]-2-pyrimidinamine, sulfate | 3.0 |
| N—Phenyl-4-(4-pyridinyl)-2-pyrimidinamine, phosphate | 3.3 |
| N—(3,5-Dimethylphenyl)-4-(2-furanyl)-2-pyrimidinamine | 0.7 |
| N—(3,5-Dimethylphenyl)-4-(2-thienyl)-2-pyrimidinamine | 4.3 |
| N—(2,4-Difluorophenyl)-4-(4-pridinyl)-2-pyrimidinamine | <48 |
| N—(2,4-Difluorophenyl)-4-(3-pyridinyl)-2-pyrimidinamine | <48 |
| N—(3-Methylphenyl)-4-(5-methyl-2-thienyl)-2-pyrimidinamine | 1.4 |
| N—(2,6-Difluorophenyl)-4-(4-pyridinyl)-2-pyrimidinamine | 2.9 |
| 4-(4-Pyridinyl)-N—[3-(trifluoromethyl)phenyl]-2-pyrimidinamine, sulfate | <48 |
| N—(4-Methoxyphenyl)-4-(3-pyridinyl)-2-pyrimidinamine, sulfate | <48 |
| N—Phenyl-4-(3-pyridinyl)-2-pyrimidinamine, sulfate | 3.0 |
| 4-(3-Pyridinyl)-N—[3-(trifluoromethyl)phenyl]-2-pyrimidinamine, sulfate | 2.6 |
| N—Phenyl-4-(4-pyridinyl)-2-pyrimidinamine, dihydrochloride | 3.0 |
| N—[4-(1,1-Dimethylethyl)phenyl]-4-(3-pyridinyl)-2-pyrimidinamine | 0.7 |
| N—(2,6-Difluorophenyl)-4-(3-pyridinyl)-2-pyrimidinamine | 22.0 |
| N—(4-Ethylphenyl)-4-(5-methyl-2-thienyl)-2-pyrimidinamine | 36.3 |
| N—[(3,4-Dimethylphenyl)methyl]-4-(2-pyridinyl)-2-pyrimidinamine | 39.8 |
| N—(3,5-Dimethylphenyl)-4-(3-pyridinyl)-2-pyrimidinamine, sulfate | 3.0 |
| N—(3,5-Dimethylphenyl)-4-(3-pyridinyl)-2-pyrimidinamine, phosphate | 3.0 |
| N—(3-Methylphenyl)-4-(1H—pyrrol-2-yl)-2-pyrimidinamine | 11.1 |
| 4-(5-Methyl-2-furanyl)-N—(3-methylphenyl)-2-pyrimidinamine | 2.0 |
| 4-Methyl-6-(5-methyl-2-thienyl)-N—phenyl-2-pyrimidinamine | 24.8 |
| N—[4-(Dimethylamino)phenyl]-4-(4-pyridinyl)-2-pyrimidinamine | 3.8 |
| N—(3-Methoxyphenyl)-4-(4-pyridinyl)-2-pyrimidinamine | 0.4 |
| N—(3-Methoxyphenyl)-4-(2-pyridinyl)-2-pyrimidinamine | 0.2 |
| N—[4-(Dimethylamino)phenyl]-4-(2-pyridinyl)-2-pyrimidinamine | 2.7 |
| N—(3-Methoxyphenyl)-4-(3-pyridinyl)-2-pyrimidinamine | 0.3 |
| N—(3,5-Dimethylphenyl)-4-(3-pyridinyl)-2-pyrimidinamine | 0.8 |
| 4-[[4-(3-Pyridinyl)-2-pyrimidinyl]amino]-benzoic acid, ethyl ester | 12.4 |
| N,N—Dimethyl-N'—[4-(3-pyridinyl)-2-pyrimidinyl]-1,4-benzenediamine | 3.7 |
| 4-(2,5-Dimethyl-3-furanyl)-N—phenyl-2-pyrimidinamine | 2.0 |
| N,N—Dimethyl-N'—[4-(4-pyridinyl)-2-pyrimidinyl)benzenediamine, trihydrochloride | 0.4 |
| 4-(2,5-Dimethyl-3-furanyl)-N—(3-methylphenyl)-2-pyrimidinamine | 28.5 |
| 4-(2,5-Dimethyl-3-furanyl)-N—(3,5-dimethylphenyl-2-pyrimidinamine | 4.1 |
| N,N—Dimethyl-N'—[4-(2-pyridinyl)-2-pyrimidinyl]-1,4-benzenediamine, dihydrochloride | 4.4 |
| 4-(2,5-Dimethyl-3-furanyl)-N—(4-ethylphenyl)-2-pyrimidinamine | 19.2 |
| N,N—Dimethyl-N'—[4-(3-pyridinyl)-2-pyrimidinyl]-1,3-benzenediamine | 1.7 |
| 3-[[4-(2-Pyridinyl)-2-pyrimidinyl]amino]benzoic acid, ethyl ester | 3.0 |
| N,N—Dimethyl-N'—[4-(2-pyridinyl)-2-pyrimidinyl]-1,3-benzenediamine | 0.5 |
| 4-[[4-(3-Pyridinyl)-2-pyrimidinyl]amino]phenol | 5.1 |
| 3-[[4-(3-Pyridinyl)-2-pyrimidinyl]amino]benzoic acid, ethyl ester | 20.3 |
| N—(4-Methoxyphenyl)-4-(3-pyridinyl)-2-pyrimidinamine, phosphate | 3.2 |
| N—(3,5-Dimethylphenyl)-4-(2-pyridinyl)-2-pyrimidinamine, sulfate | 0.6 |
| N—[4-(2-Propenyloxy)phenyl]-4-(3-pyridinyl)-2-pyrimidinamine | 0.8 |
| N—[4-[2-(Dimethylamino)ethoxy]phenyl]-4-(3-pyridinyl)-2-pyrimidinamine | 0.5 |
| N—Phenyl-4-(3-pyridinyl)-2-pyrimidinamine, phosphate | 2.7 |
| N'—[4-(2-Furanyl)-2-pyrimidinyl]-N,N—dimethyl-1,4-benzenediamine | 1.9 |
| N,N—Dimethyl-N'—[4-(2-thienyl)-2-pyrimidinyl]-1,4-benzenediamine | 0.6 |
| N'—[4-(2,5-Dimethyl-3-furanyl)-2-pyrimidinyl]-N,N—dimethyl-1,4-benzenediamine | 4.9 |

TABLE I-continued
Inhibition of Histamine Release from Immunologically Stimulated Human Basophils

| Compound | IC$_{50}$($\mu$M) |
|---|---|
| N,N—Dimethyl-N'—[4-(3-methyl-2-thienyl)-2-pyrimidinyl]-1,4-benzenediamine | 1.8 |
| N—(3,5-Dimethylphenyl)-4-(2-pyridinyl)-2-pyrimidinamine, phosphate | 0.3 |
| N,N—Dimethyl-N'—[4-(3-pyridinyl)-2-pyrimidinyl]-1,4-benzenediamine, trihydrochloride | 1.5 |
| N,N—Dimethyl-N'—[4-(4-pyridinyl)-2-pyrimidinyl]-1,3-benzenediamine | 3.5 |
| N,N—Dimethyl-N'—[4-methyl-6-(4-pyridinyl)-2-pyrimidinyl]-1,4-benzenediamine | 37.7 |
| N—[4-3-Dimethylamino)propoxy]phenyl]-4-(3-pyridinyl)-2-pyrimidinamine | 0.5 |
| N—[4-[2-Diethylamino)ethoxy]phenyl]-4-(3-pyridinyl)-2-pyrimidinamine | 0.2 |
| N—[4-[2-Dimethylamino)ethoxy]phenyl]-4-(3-pyridinyl)-2-pyrimidinamine, hydrochloride | 0.5 |
| 4-[[4-(3-Pyridinyl)-2-pyrimidinyl]amino]benzoic acid | 7.6 |
| N,N—Dimethyl-N'—[4-(2-pyridinyl)-2-pyrimidinyl]-1,3-benzenediamine, dihydrochloride | 0.5 |
| N,N—Dimethyl-N'—[4-(2-pyridinyl)-2-pyrimidinyl]-1,3-benzenediamine, trihydrochloride | 1.0 |
| N—(3,5-Dimethylphenyl)-4-(2-furanyl)-5-methyl-2-pyrimidinamine | <24 |
| N,N—Dimethyl-N'—[4-(4-pyridinyl)-2-pyrimidinyl]-1,3-benzenediamine, dihydrochloride | 0.5 |
| N'—[4-(2-Furanyl)-5-methyl-2-pyrimidinyl]-N,N—dimethyl-1,4-benzenediamine | 6.1 |
| 4-(2-Furanyl)-5-methyl-N—phenyl-2-pyrimidinamine, sulfate | 5.0 |
| N'—[4-(2-Benzofuranyl)-2-pyrimidinyl]-N,N—dimethyl-1,4-benzenediamine | 5.6 |
| 4-Methyl-N—phenyl-6-(2-pyridinyl)-2-pyrimidinamine | 26.8 |
| 4-[[4-(4-(Pyridinyl)-2-pyrimidinyl]amino]phenol | 3.3 |
| N—[4-[2-(Dimethylamino)ethoxy]phenyl]-4-(4-pyridinyl)-2-pyrimidinamine | 1.5 |
| N—[4-[2-(Dimethylamino)ethoxy]phenyl]N',N'—dimethyl-N—[4-(4-pyridinyl)-2-pyrimidinyl]-1,2-ethanediamine | 9.1 |
| N—[4-3-Dimethylamino)propoxy]phenyl]-4-(4-pyridinyl)-2-pyrimidinamine | 1.3 |
| N—[4-[2-(Diethylamino)ethoxy]phenyl]-4-(4-pyridinyl)-2-pyrimidinamine | 0.2 |
| 4-[2-[(4-Methoxyphenyl)amino]-4-pyrimidinyl]-1-methylpyridinium, iodide | 33.3 |
| N,N—Dimethyl-N'—[4-(4-pyridinyl)-2-pyrimidinyl)]-1,3-benzenediamine, sulfate | 1.0 |
| N,N—Dimethyl-N'—[4-(2-thienyl)-2-pyrimidinyl]-1,3-benzenediamine | 2.4 |
| N,N—Dimethyl-N'—[4-(5-methyl-2-furanyl)-2-pyrimidinyl]-1,3-benzenediamine | 1.6 |
| N'—[4-(2,5-Dimethyl-3-furanyl)-2-pyrimidinyl]-N,N—dimethyl-1,3-benzenediamine | <24 |
| N—[2-(Diethylamino)ethyl]-4-[[4-(3-pyridinyl)-2-pyrimidinyl]amino]benzamide | 0.8 |
| 4-[[4-(4-Pyridinyl)-2-pyrimidinyl]amino]phenoxy]acetic acid, ethyl ester | 5.8 |
| N,N—Diethyl-N'—[4-(4-pyridinyl)-2-pyrimidinyl]-1,4-benzenediamine | 1.1 |
| N,N—Dimethyl-N'—[4-methyl-6-(2-pyridinyl)-2-pyrimidinyl]-1,4-benzenediamine | 31.8 |
| N—[4-(1H—Imidazol-1-yl)phenyl]-4-(4-pyridinyl)-2-pyrimidinamine | 12.3 |
| N—[4-(4-Pyridinyl)-2-pyrimidinyl]-1,4-benzenediamine, hydrochloride | 3.0 |
| N,N—Diethyl-N'—[4-(3-pyridinyl)-2-pyrimidinyl]-1,4-benzenediamine | 1.7 |
| N—[4-(1H—Imidazol-1-yl)phenyl]-4-(3-pyridinyl)-2-pyrimidinamine | 1.3 |
| 1-[4-[[4-(3-Pyridinyl)-2-pyrimidinyl]amino]phenyl]ethanone, oxime | 11.4 |
| 1-[4-[[4-(3-Pyridinyl)-2-pyrimidinyl]amino]phenyl]ethanone, O—methyloxime | 5.1 |
| N,N—Diethyl-N'—[4-(2-pyridinyl)-2-pyrimidinyl]-1,4-benzenediamine | 10.1 |
| N—[4-(1H—Imidazol-1-yl)phenyl]-4-(2-pyridinyl)-2-pyrimidinamine | 1.8 |
| 4-(2-Furanyl)-N—[4-(1H—imidazol-1-yl)phenyl]-2-pyrimidinamine | 2.2 |
| N—Methyl-4-[[4-(3-pyridinyl)-2-pyrimidinyl]amino]-benzamide | 4.6 |
| N,N—Dimethyl-N'—[4-(5-methyl-2-thienyl)-2-pyrimidinyl]-1,3-benzenediamine | 5.7 |
| N,N—Dimethyl-N'—[4-(3-thienyl)-2-pyrimidinyl]-1,4-benzenediamine | 2.1 |
| N—[1-[4-[[4-(3-Pyridinyl)-2-pyrimidinyl]amino]phenyl]ethyl]formamide | 0.4 |
| N—[4-(1-Aminoethyl)phenyl]-4-(3-pyridinyl)-2-pyrimidinamine, trihydrochloride | 0.8 |
| 4-[[4-(3-Pyridinyl)-2-pyrimidinyl]amino]benzenesulfonamide | 0.2 |
| N—(3-Chlorophenyl)-4-(4-pyridinyl)-2-pyrimidinamine | 3.1 |
| N—(3-Chlorophenyl)-4-(3-pyridinyl)-2-pyrimidinamine | 1.5 |
| N—(3-Methoxyphenyl)-4-(3-thienyl)-2-pyrimidinamine | 1.7 |
| N—Methyl-N—[4-[[4-(3-pyridinyl)-2-pyrimidinyl]amino]phenyl]acetamide | 1.1 |
| N—Methyl-N—[4-[[4-(4-pyridinyl)-2-pyrimidinyl]amino]phenyl]acetamide | 0.1 |
| N—Methyl-N—[4-[[4-(2-pyridinyl)-2-pyrimidinyl]amino]phenyl]acetamide | 0.6 |
| [4-(2-Furanyl)-N—(3-methoxyphenyl)-2-pyrimidinamine | 0.3 |
| 4-(2-Benzofuranyl)-N—(3-methoxyphenyl)-2-pyrimidinamine | 1.2 |
| Oxo[phenyl[4-(4-pyridinyl)-2-pyrimidinyl]amino]acetic acid, ethyl ester | 2.1 |
| N—[4-[[4-(4-Pyridinyl)-2-pyrimidinyl]amino]phenyl]acetamide | 5.3 |
| N,N—Dimethyl-N'—[4-(2-furanyl)-5-methyl-2-pyrimidinyl]-1,3-benzenediamine | 40 |
| N—[4-[[4-(3-Pyridinyl)-2-pyrimidinyl]amino]phenyl]acetamide | 3.6 |
| 4-[[4-(2-Pyridinyl)-2-pyrimidinyl]amino]benzenesulfonamide | 4.5 |
| N—[4-[[4-(2-Pyridinyl)-2-pyrimidinyl]amino]phenyl]acetamide | 1.5 |
| N—(3-Methoxyphenyl)-4-(2-thienyl)-2-pyrimidinamine | 0.9 |
| N—[4-(4-Methyl-1-piperazinyl)phenyl]-4-(3-pyridinyl)-2-pyrimidinamine | 1.5 |
| N—(3-Methoxyphenyl)-4-(5-methyl-2-thienyl)-2-pyrimidinamine | 2.3 |
| N—(3-Chlorophenyl)-4-(2-pyridinyl)-2-pyrimidinamine | 1.3 |
| 4-(2-Furanyl)-N—[4-(4-methyl-1-piperazinyl)phenyl]-2-pyrimidinamine | 1.8 |
| N—[4-(4-Methyl-1-piperazinyl)phenyl]-4-(4-pyridinyl)-2-pyrimidinamine | 0.6 |
| N—(3-Methoxyphenyl)-4-(2,5-dimethyl-3-furanyl)-2-pyrimidinamine | 5.8 |
| N—[4-(2-Pyridinyl)-2-pyrimidinyl]-1,4-benzenediamine, dihydrochloride | 1.0 |
| N—(3-Fluorophenyl)-4-(4-pyridinyl)-2-pyrimidinamine | 0.7 |
| N—(3-Fluorophenyl)-4-(3-pyridinyl)-2-pyrimidinamine | 3.3 |
| N—(3-Fluorophenyl)-4-(2-pyridinyl)-2-pyrimidinamine | 0.9 |
| 1-[3-[[4-(3-Pyridinyl)-2-pyrimidinyl]amino]phenyl]ethanone | 4.1 |
| N—Methyl-N'—[4-(3-pyridinyl)-2-pyrimidinyl]-1,4-benzenediamine | 2.1 |
| N—[4-(1-Methylethyl)phenyl]-4-(3-pyridinyl)-2-pyrimidinamine | 1.1 |
| N—Methyl-N'—[4-(2-pyridinyl)-2-pyrimidinyl]-1,4-benzenediamine | 1.4 |
| N—(3-Ethylphenyl)-4-(3-pyridinyl)-2-pyrimidinamine | 1.7 |
| N—(3-Ethylphenyl)-4-(2-pyridinyl)-2-pyrimidinamine | 1.4 |
| 3-[[4-(2-Pyridinyl)-2-pyrimidinyl]amino]ben- | 0.7 |

TABLE I-continued

Inhibition of Histamine Release from
Immunologically Stimulated Human Basophils

| Compound | IC$_{50}$($\mu$M) |
|---|---|
| 3-[[4-(3-Pyridiny)-2-pyrimidinyl]amino]benzenesulfonamide | 0.2 |
| N—[4-(1,1-Dimethylethyl)phenyl]-4-(2-thienyl)-2-pyrimidinamine | 4.6 |
| N,N—Diethyl-N'—[4-(2-furanyl)-2-pyrimidinyl]-1,4-benzenediamine | 3.4 |
| 3-[[4-(4-Pyridinyl)-2-pyrimidinyl]amino]-benzenesulfonamide | 0.5 |
| N,N—Dimethyl-N'—[4-(4-pyridinyl)-2-pyrimidinyl]-1,2-benzenediamine, fumarate | 36.2 |
| 2-[1-[4-[[4-(3-Pyridinyl)-2-pyrimidinyl]amino]phenyl]ethylidene]hydrazinecarboxamide | 8.1 |
| N—[4-[2-[bis(1,1-Dimethylethyl)amino]ethoxy]phenyl]-4-(3-pyridinyl)-2-pyrimidinamine | 4.6 |
| α-Methyl-4-[[4-(3-pyridinyl)-2-pyrimidinyl]amino]benzenemethanol | 4.5 |
| N—[1-[3-[[4-(3-Pyridinyl)-2-pyrimidinyl]amino]phenyl]ethyl]formamide | 4.6 |
| N—[3-[[4-(4-Pyridinyl)-2-pyrimidinyl]amino]phenyl]acetamide | 2.1 |
| N—[3-[[4-(3-Pyridinyl)-2-pyrimidinyl]amino]phenyl]acetamide | 5.0 |
| N—[4-(3-Pyridinyl)-2-pyrimidinyl]-1,3-benzenediamine, dihydrochloride | 0.4 |
| N,N—Diethyl-N'—[4-(5-methyl-2-furanyl)-2-pyrimidinyl]1,4-benzenediamine | 28.0 |
| N—(3-Methoxyphenyl)-4-(5-methyl-2-furanyl)-2-pyrimidinamine | 1.2 |
| N—[3-[[4-(2-Pyridinyl)-2-pyrimidinyl]amino]phenyl]acetamide | 0.3 |
| N—[3-(1H—Imidazol-1-yl)phenyl]-4-(2-pyridinyl)-2-pyrimidinamine | 0.1 |
| N—[4-(4-pyridinyl)-2-pyrimidinyl]-1,3-benzenediamine | 1.0 |
| N—[2-Methyl-4-[[4-(4-pyridinyl)-2-pyrimidinyl]amino]phenyl]acetamide | 1.2 |
| 2-Methyl-N—[4-(4-pyridinyl)-2-pyrimidinyl]-1,4-benzenediamine, dihydrochloride | 0.9 |
| N—[4-(2-Pyridinyl)-2-pyrimidinyl]-1,3-benzendiamine | 0.2 |
| N—[4-[[4-(5-Methyl-2-thienyl)-2-pyrimidinyl]amino]phenyl]acetamide | 0.3 |
| N—[3-(1-Aminoethyl)phenyl]-4-(3-pyridinyl)-2-pyrimidinamine, trihydrochloride | 5.1 |
| N—[3-[2-(Diethylamino)ethoxy]phenyl]-4-(3-pyridinyl)-2-pyrimidinamine | 2.8 |
| N—(2-Methoxyphenyl)-4-(3-pyridinyl)-2-pyrimidinamine | 9.8 |
| N—[4-[[4-(2-Thienyl)-2-pyrimidinyl]amino]phenyl]acetamide | 0.2 |
| N—[2-Methyl-4-[4-(3-pyridinyl)-2-pyrimidinyl]phenyl]acetamide | 1.8 |
| N'—[4-(2-Benzofuranyl)-2-pyrimidinyl]-N,N—diethyl-1,4-benzenediamine | 6.2 |
| N—[4-[[4-(2-Furanyl)-2-pyrimidinyl]amino]phenyl]acetamide | 0.7 |
| N—[4-(1H—Imidazol-1-yl)-3-(trifluoromethyl)phenyl]-4-(4-pyridinyl)-2-pyrimidinamine | 0.4 |
| N—[3-(1H—Imidazol-1-yl)phenyl]-4-(3-pyridinyl)-2-pyrimidinamine | 0.1 |
| 2-[[4-(3-Pyridinyl)-2-pyrimidinyl]amino]-phenol | 23.5 |
| 4-(2-Furanyl)-N—[3-(1H—imidazol-1-yl)phenyl]-2-pyrimidinamine | 0.8 |
| N—[3-[2-(Diethylamino)ethoxy]phenyl]-4-(2-furanyl)-2-pyrimidinamine | 1.3 |
| N—[4-(1H—Imidazol-1-yl)-3-(trifluoromethyl)phenyl]-4-(2-pyridinyl)-2-pyrimidinamine | 1.6 |
| N—[3-[2-(Diethylamino)ethoxy]phenyl]-4-(2-thienyl)-2-pyrimidinamine | 0.6 |
| N—[3-[2-(Diethylamino)ethoxy]phenyl]-4-(4-pyridinyl)-2-pyrimidinamine | 0.7 |
| N—[4-(4-Pyridinyl)-2-pyrimidinyl]-1,4-benzenediamine | 2.4 |
| N—[3-(1H—Imidazol-1-yl)phenyl]-4-(4-pyridinyl)-2-pyrimidinamine | 0.4 |
| N—[3-(1H—Imidazol-1-yl)phenyl]-4-(2-thienyl)-2-pyrimidinamine | 0.2 |

TABLE I-continued

Inhibition of Histamine Release from
Immunologically Stimulated Human Basophils

| Compound | IC$_{50}$($\mu$M) |
|---|---|
| pyrimidinamine | |

The ability of these compounds to inhibit lipoxygenase activity in terms of the suppression of the release and biosynthesis of leukotriene B4(LTB4) and 5-hydroxy-eicosatetraenoic acid (5-HETE) was measured as follows.

In this assay $3 \times 10^7$ peritoneal neutrophils derived from guinea pigs were incubated at 37° C. in Dulbeccos buffer containing 50 mM tris buffer (pH 7.4). Five minutes before the addition of 100 $\mu$M arachidonic acid and 20 $\mu$M calcium ionophore (A23187), control vehicle or the test compounds were added to the neutrophils at a concentration of 10 $\mu$g/ml.

Three minutes after the addition of arachidonic acid and calcium ionophore the total lipid was partitioned into chloroform after adjusting the pH to 3 with citric acid and the addition of equal parts of methanol and chloroform.

The 5-HETE and LTB4 were resolved by HPLC using a 5 $\mu$m 4×25 cm octadecyl silica column (IBM Instruments) with 70–80% methanol in water adjusted to pH 3.0 with acetic acid. As the mobile phase was pumped at 1.0 ml/minute, LTB4 and 5-HETE were detected by absorbance of 270 and 236 nm, respectively.

LTB4 and 5-HETE were quantitated by comparison with the control and the results were expressed as a percent of control. The lower the percentage, the more active the compound.

The results of this test on representative compounds of this invention appear in Table II.

TABLE II

Inhibition of Neutrophil Lipoxygenase from
Immunologically Stimulated Guinea Pig Neutrophiles

| Compound | % Inhibition | |
|---|---|---|
|  | LTB4 | 5-HETE |
| 4-(3-Pyridinyl)-N—[3-trifluoromethyl)phenyl]-2-pyrimidinamine | 58.1 | |
| N—(4-Acetylphenyl)-4-(3-pyridinyl)-2-pyrimidinamine | | 37.0 |
| N—(4-Fluorophenyl)-4-(2-pyridinyl)-2-pyrimidinamine | | 45.0 |
| N—(4-Methylphenyl)-4-(4-pyridinyl)-2-pyrimidinamine | | 45.0 |
| N—(4-Fluorophenyl)-4-(4-pyridinyl)-2-pyrimidinamine | | 53.0 |
| 4-(3-Pridinyl)-N—[3-trifluoromethyl)phenyl]-2-pyrimidinamine | | 58.0 |
| N—Phenyl-4-(4-pyridinyl)-2-pyrimidinamine | | 58.0 |
| N—(3-Methylphenyl)-4-(3-pyridinyl)-2-pyrimidinane | | 40.0 |
| N—[4-Ethylphenyl)-4-(4-pyridinyl)-2-pyrimidinamine | 33.9 | 41.0 |
| N—(4-Ethylphenyl)-4-(2-pyridinyl)-2-pyrimidinaine | 29.5 | 41.0 |
| 4-(2-Furanyl)-N—(3-methylphenyl)-2-pyrimidinamine | 7.4 | 3.0 |
| N—[4-(4-Methyl-1-piperazinyl)phenyl]-4-(2-thienyl)-2-pyrimidinamine | 48.0 | |
| N—(4-Ethylphenyl)-4-(6-methyl-3-pyridinyl)-2-pyrimidinamine | 53.4 | 54.0 |
| N—(3-Methylphenyl)-4-pyrazinyl-2-pyrimidinamine | | 50.0 |
| N—(3-Ethylphenyl)-4-(4-pyridinyl)-2-pyrimidinamine | 36.4 | 28.7 |
| N—(2,3-Dimethylphenyl)-4-(4-pyridinyl)-2-pyrimidinamine | 58.4 | |
| N—Phenyl-4-(3-thienyl)-2-pyrimidinamine | | 56.0 |

TABLE II-continued
Inhibition of Neutrophil Lipoxygenase from Immunologically Stimulated Guinea Pig Neutrophiles

| Compound | % Inhibition LTB4 | % Inhibition 5-HETE |
|---|---|---|
| N—(3-Methylphenyl)-4-(3-thienyl)-2-pyrimidinamine | | 48.0 |
| N—(4-Ethylphenyl)-4-(3-thienyl)-2-pyrimidinamine | | 56.0 |
| N—(2,4-Dimethylphenyl)-4-(2-pyridinyl)-2-pyrimidinamine | | 54.0 |
| N—(3,5-Dimethylphenyl)-4-(4-pyridinyl)-2-pyrimidinamine | 53.1 | 54.0 |
| N—(2-Methoxyphenyl)-4-(4-pyridinyl)-2-pyrimidinamine | 17.4 | 21.0 |
| N—(2,5-Dimethoxyphenyl)-4-(4-pyridinyl)-2-pyrimidinamine | 43.2 | 47.0 |
| N—(2,4-Dimethylphenyl)-4-(4-pyridinyl)-2-pyrimidinamine | 37.0 | 43.0 |
| N—(2-Methoxy-5-methylphenyl)-4-(2-pyridinyl)-2-pyrimidinamine | | 54.0 |
| 4-(4-Pyridinyl)-N—(2,4,6-trimethylphenyl)-2-pyrimidinamine | 53.6 | |
| 4-(2-Furanyl)-N—(4-methoxyphenyl)-2-pyrimidinamine | | 44.0 |
| 4-(2-Furanyl)-N—[3-trifluoromethyl)phenyl]-2-pyrimidinamine | 45.0 | 49.0 |
| N—(4-Fluorophenyl)-4-(2-furanyl)-2-pyrimidinamine | 33.0 | |
| N—Phenyl-4-(4-pyridinyl)-2-pyrimidinamine, compound with 2-hydroxy-1,2,3-propanetricarboxylate (2:1) | 58.0 | |
| N—[3,4-Dimethylphenyl]methyl]-4-(4-pyridinyl)-2-pyrimidinamine | 24.0 | 36.0 |
| N—Phenyl-4-(4-pyridinyl)-2-pyrimidinamine, sulfate | 56.0 | |
| 4-(2-Benzofuranyl)-N—(3-methylphenyl)-2-pyrimidinamine | 46.1 | |
| N—(4-Ethylphenyl)-4-(4-pyridinyl)-2-pyrimidinamine | | 19.0 |
| N—(3,4-Dimethylphenyl)-4-(4-pyridinyl)-2-pyrimidinamine | | 19.0 |
| N—(3,4-Dimethylphenyl)-4-(2-pyridinyl)-2-pyrimidinamine | 17.3 | 35.0 |
| N—(4-Fluorophenyl)-4-(3-theinyl)-2-pyrimidinamine | 51.6 | |
| 4-(10H—Phenothiazin-2-yl)-N—phenyl-2-pyrimidinamine | | 48.0 |
| 4-(1H—Indol-3-yl)-N—phenyl-2-pyrimidinamine | 41.2 | 39.0 |
| N—(2-Methoxy-5-methylphenyl)-4-(4-pyridinyl)-2-pyrimidinamine | 44.7 | 37.0 |
| N—(3-Methylphenyl)-4-(1-methyl-1H—pyrrol-2-yl)-2-pyrimidinamine | | 60.0 |
| 4-(1-Methyl-1H—pyrrol-2-yl)N—phenyl-2-pyridinamine | | 57.0 |
| N—(4-Ethylphenyl)-4-(1H—indol-3-yl)-2-pyridinamine | 56.5 | |
| N—[1,1'-Biphenyl]-4-yl-(4-pyridinyl)-2-pyrimidinamine | 37.1 | 45.0 |
| 4-[[4-(4-Pyridinyl)-2-pyrimidinyl]-amino]benzoic acid, methyl ester | 45.2 | 47.0 |
| N—(3-Methylphenyl)-4-(4-quinolinyl)-2-pyrimidinamine | 16.0 | |
| N—Phenyl-4-(4-quinolinyl)-2-pyrimidinamine | 46.4 | 57.0 |
| N—(4-Ethylphenyl)-4-(4-quinolinyl)-2-pyrimidinamine | | 58.0 |
| N—(3,5-Dimethylphenyl)-4-(2-furanyl)-2-pyrimidinamine | 56.1 | |
| N—[(1,1-Dimethylethyl)phenyl]-4-(4-pyridinyl)-2-pyrimidinamine | 47.8 | 54.0 |
| N—Methyl-N—phenyl-4-(2-pyridinyl)-2-pyridinamine | 58.1 | 54.0 |
| N—Phenyl-4-(1H—pyrrol-2-yl)-2-pyrimidinamine | 55.4 | |
| N—(4-Ethylphenyl)-4-(1H—pyrrol-2-yl)-2-pyrimidinamine | 32.6 | 54.0 |
| 4-(3-Pyridinyl)-N—[3-(trifluoromethyl)phenyl]-2-pyrimidinamine sulfate | 37.3 | 49.0 |
| N—Phenyl-4-(4-pyridinyl)-2-pyrimidinamine, dihydrochloride | 48.0 | 43.0 |
| 4-(3-Methyl-2-thienyl)-N—phenyl-2-pyrimidinamine | | 59.0 |
| 4-(5-Methyl-2-furanyl)-N—(3-methylphenyl)-2-pyrimidinamine | 59.6 | |
| 4-Methyl-6-(5-methyl-2-thienyl)-N—phenyl-2-pyrimidinamine | 42.3 | 52.0 |
| N—[4-(Dimethylamino)phenyl]-4-(4-pyridinyl)-2-pyrimidinamine | 16.6 | 12.4 |
| N—(3-Methoxyphenyl)-4-(4-pyridinyl)-2-pyridinamine | 31.2 | 50.0 |
| N—[4-(Dimethylamino)phenyl]-4-(2-pyridinyl)-2-pyrimidinamine | 20.1 | 17.2 |
| N—(3,5-Dimethylphenyl)-4-(3-pyridinyl)-2-pyrimidinamine | 50.7 | 56.0 |
| 4-[[4-(3-Pyridinyl)-2-pyrimidinyl]amino]benzoic acid, ethyl ester | 35.8 | 47.0 |
| N,N—Dimethyl-N—'[4-(3-pyridinyl)-2-pyrimidinyl]-1,4-benzenediamine | 43.4 | 34.0 |
| 4-(2,5-Dimethyl-3-furanyl)-N—phenyl-2-pyridinamine | 46.9 | 56.0 |
| N,N—Dimethyl-N'—[4-(4-pyridinyl)-2-pyrimidinyl]-1,4-benzenediamine, trihydrochloride | 40.7 | 37.0 |
| N,N—Diemthyl-N'—(2-pyridinyl)-2-pyrimidinyl]-1,4-benzenediamine, dihydrochloride | 37.6 | 39.0 |
| 4-[[4-(3-Pyridinyl)-2-pyrimidinyl]amino]phenol | | 30.0 |
| 3-[[4-(3-Pyridinyl)-2-pyrimidinyl]amino]benzoic acid, ethyl ester | 36.1 | 50.0 |
| N—(3,5-Dimethylphenyl)-4-(2-pyridinyl)-2-pyrimidinamine, sulfate | 50.0 | |
| N—[4-(2-Propenyloxy)phenyl]-4-(3-pyridinyl)-2-pyrimidinamine | 34.1 | |
| N'—4-(2-Furnayl)-2-pyrimidinyl]-N,N—dimethyl-1,4-benzenediamine | 16.9 | 16.9 |
| N,N—Dimethyl-N'—[4-(2-thienyl)-2-pyrimidinyl]-1,4-benzenediamine | 49.8 | 17.8 |
| N'—[4-(2,5-Dimethyl-3-furanyl)-2-pyrimidinyl]-N,N—dimethyl-1,4-benzenediamine | 21.6 | 17.0 |
| N,N—Dimethyl-N'—[4-(3-methyl-2-thienyl)-2-pyrimidinyl]-1,4-benzenediamine | 16.4 | 13.6 |
| N,N'—[4-(3-pyridinyl)-2-pyrimidinyl]-1,4-benzenediamine, trihydrochloride | 46.8 | 42.0 |
| N,N—Dimethyl-N'—[4-(4-pyridinyl)-2-pyrimidinyl]-1,3-benzenediamine | 51.1 | |
| N,N-Dimethyl-N'—[4-methyl-6-(4-pyridinyl)-2-pyrimidinyl]-1,4-benzenediamine | 1.6 | 10.0 |
| N—(3,5-Dimethylphenyl)-4-methyl-6-(3-pyridinyl)-2-pyrimidinamine | 32.7 | 40.0 |
| N'—[4-(2-Furanyl)-5-methyl-2-pyrimidinyl]-N,N—dimethyl-1,4-benzenediamine | 3.6 | |
| 4-(2-Furanyl)-5-methyl-N—phenyl-2-pyrimidinamine, sulfate | 52.4 | |
| N'—[4-(2-Benzofuranyl)-2-pyrimidinyl]-N,N—dimethyl-1,4-benzenediamine | 22.9 | 30.0 |
| 4-Methyl-N—phenyl-6-(2-pyridinyl)-2-pyrimidinamine | 30.3 | 42.0 |
| 4-[[4-(4-Pyridinyl)-2-pyrimidinyl]-amino]phenol | | 36.0 |
| N—(4-Methoxyphenyl)-N—methyl-4-(4-pyridinyl-2-pyrimidinamine | 57.4 | |
| N,N—Dimethyl-N'—[4-(2-thienyl)-2-pyrimidinyl]-1,3-benzenediamine | 39.6 | 50.0 |
| N,N—Dimethyl-N'—[4-(5-methyl-2-furanyl)-2-pyrimidinyl]-1,3-benzenediamine | 31.1 | 37.7 |
| N—Methyl-N'—(2-pyridinyl)-2-pyrimidinyl]-1,4-benzenediamine | 24.1 | 53.6 |
| N—[1-3-[[4-(3-Pyridinyl)-2-pyrimidinyl]amino]phenyl]ethyl]formamide | 34.0 | |
| N—[4-[[4-(5-Methyl-2-thienyl)-2-pyrimidinyl]amino]phenyl]acetamide | 51.0 | 46.0 |
| N'—[4-(2-Benzofuranyl)-2-pyrimidinyl]-N,N—diethyl-1,4-benzenediamine | 51.0 | 45.0 |
| N—[4-(1H—Imidazol-1-yl)-3-(trifluoromethyl)phenyl]-4-(4-pyridinyl)-2-pyrimidinamine | 20.0 | 16.0 |
| N—[4-(5-Methyl-2-thienyl)-2-pyrimidinyl]- | 47.0 | 28.0 |

TABLE II-continued

Inhibition of Neutrophil Lipoxygenase from
Immunologically Stimulated Guinea Pig Neutrophiles

| Compound | % Inhibition | |
|---|---|---|
| | LTB4 | 5-HETE |
| 1,4-benzenediamine, dihydrochloride N—]3-(1H—Imidazol-1-yl)phenyl]-4-(3-pyridinyl)-2-pyrimidinamine | 50.0 | 51.0 |
| N—[3-(1H—Imidazolyl)phenyl]-4-(2-thienyl)-2-pyrimidinamine | 50.0 | 39.0 |
| N—[4-(2-Furanyl)-2-pyrimidinyl]-1,4-benzenediamine, dihydrochloride | | 54.0 |
| N—[4-(1H—Imidazol-1-yl)-3-(trifluoromethyl)phenyl]-4-(2-pyridinyl)-2-pyrimidinamine | | 19.0 |
| 4-[[4-(2-Furanyl)-2-pyrimidinyl]amino]-benzenesulfonamide | | 47.0 |

The novel compounds of the present invention are effective as antiasthmatic agents in mammals when administered in amounts ranging from about 0.1 mg to about 100 mg/kg of body weight per day. A preferred dosage regimen for optimum results would be from about 0.1 mg to about 25 mg/kg of body weight per day, and such dosage units are employed that a total of from about 7 mg to about 1.8 g of the active compound for a subject of about 70 kg of body weight are administered in a 24 hour period. This dosage regimen may be adjusted to provide the optimum therapeutic response. For example, several divided doses may be administered daily or the dose may be proportionally reduced as indicated by the exigencies of the therapeutic situation. A decided practical advantage is that these active compounds may be administered in any convenient manner such as by the oral, aerosol, intravenous, intramuscular, or subcutaneous routes.

The active compounds may be orally administered, for example, with an inert diluent or with an assimilable edible carrier, or they may be enclosed in hard or soft shell gelatin capsules, or they may be compressed into tablets or they may be incorporated directly with the food of the diet. For oral therapeutic administration, these active compounds may be incorporated with excipients and used in the form of ingestible tablets, buccal tablets, troches, capsules, elixirs, suspensions, syrups, wafers and the like. Such compositions and preparations should contain at least 0.1% of active compound. The percentage of the compositions and preparations may, of course, be varied and may conveniently be between about 2% to about 60% of the weight of the unit. The amount of active compound in such therapeutically useful compositions is such that a suitable dosage will be obtained. Preferred compositions or preparations according to the present invention are prepared so that an oral dosage unit form contains between about 5 and 200 mg of active compound.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen or cherry flavoring. When the dosage unit form is a capsule, it may contain, in addition to materials of the above type, a liquid carrier. Various other materials may be present as coatings or to otherwise modify the physical form of the dosage unit. For instance, tablets, pills or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts used. In addition, these active compounds may be incorporated into sustained-release preparations and formulations.

Compositions according to the present invention having the desired clarity, stability and adaptability for parenteral use are obtained by dissolving from 0.10% to 10.0% by weight of active compound in a vehicle consisting of a polyhydric aliphatic alcohol or mixtures thereof. Especially satisfactory are glycerin, propylene glycol, and polyethylene glycols. The polyethylene glycols consist of a mixture of non-volatile, normally liquid, polyethylene glycols which are soluble in both water and organic liquids and which have molecular weights of from about 200 to 1500. Although various mixtures of the aforementioned non-volatile polyethylene glycols may be employed, it is preferred to use a mixture having an average molecular weight of from about 200 to about 400.

In addition to the active compound, the parenteral solutions may also contain various preservatives which may be used to prevent bacterial and fungal contamination. The preservatives which may be used for these purposes are, for example, myristyl-gamma-picolinium chloride, benzalkonium chloride, phenethyl alcohol, p-chlorophenyl-alpha-glycerol ether, methyl and propyl parabens, and thimerosal. As a practical matter, it is also convenient to employ antioxidants. Suitable antioxidants include, for example, sodium bisulfite, sodium metabisulfite, and sodium formaldehyde sulfoxylate. Generally, from about 0.05% to about 0.2% concentrations of anti-oxidant are employed.

These compounds may also be administered by inhalation using conventional Aerosol ® formulations.

The invention will be described in greater detail in conjunction with the following specific examples.

EXAMPLE 1

4-(3-Pyridinyl)-N-[3-(trifluoromethyl)phenyl]-2-pyrimidinamine

A 7.04 g amount of 3-dimethylamino-1-(3-pyridinyl)-2-propen-1-one (U.S. Pat. No. 4,281,000) and 18.72 g of [3-(trifluoromethyl)phenyl]guanidine carbonate in 500 ml of n-propanol was heated at reflux temperature for 16 hours. The solvent was evaporated to near dryness, then water was added and the precipitate which formed was collected by filtration, then recrystallized from hexane to give 5.55 g of the desired product, mp 170°–171° C.

EXAMPLE 2

N-(4-Methoxyphenyl)-4-(3-pyridinyl)-2-pyrimidinamine

A mixture of 14.4 g of 3-dimethylamino-1-(3-pyridinyl)-2-propen-1-one and 16.1 g of 4-methoxyphenyl guanidine carbonate in 200 ml of isopropanol was heated at reflux for 20 hours. The reaction mixture was cooled, the crude product was collected by filtration and washed with water. The material was recrystallized from isopropanol to give the desired product as light yellow crystals, mp 121°–122° C.

EXAMPLE 3

N-(4-Methoxyphenyl)-4-(4-pyridinyl)-2-pyrimidinamine

A 14.4 g amount of 3-dimethylamino-1-(4-pyridinyl)-2-propen-1-one (U.S. Pat. No. 4,281,000) and 16.1 g of 4-methoxyphenylguanidine carbonate in 200 ml of isopropanol was heated at reflux for 24 hours. The solvent was evaporated to ⅓ volume, then the mixture was cooled in an ice-bath to crystallize the crude product. The product was collected by filtration and washed with water, then with isopropanol. The material was recrystallized from isopropanol/ethylene glycol monomethyl ether to give 16.7 g of the desired product as yellow crystals, mp 174°–175° C.

EXAMPLE 4

N-(4-Methoxyphenyl)-4-(2-thienyl)-2-pyrimidinamine

A mixture of 10.9 g of 3-dimethylamino-1-(2-thienyl)-2-propen-1-one (U.S. Pat. No. 4,374,988) and 11.8 g of 4-methoxyphenylguanidine carbonate in 150 ml of isopropanol was heated at reflux for 48 hours. The solution was cooled, then filtered, giving 9.0 g of the desired product as yellow crystals, mp 158°–160° C.

EXAMPLE 5

4-[[4-(4-Pyridinyl)-2-pyrimidinyl]amino]benzoic acid, methyl ester

A solution of 10.0 g of 4-guanidinobenzoic acid, hydrochloride in 310 ml of methanol was mixed with 6.0 ml (9.68 g) of thionyl chloride at 0° C. for 15 minutes, then stirred for one hour at room temperature and then heated at reflux for 16 hours. The solvent was removed in vacuo and the solid was washed with ether and air dried to give 11.4 g of white crystals (A).

The above procedure was repeated using 20.0 g of 4-guanidinobenzoic acid, 11.9 ml (19.4 g) of thionyl chloride and 600 ml of methanol to give 22.6 g of white crystals (B).

The products (A) and (B) were combined and recrystallized from absolute ethanol. The product was washed with cold absolute ethanol and air dried giving 26.2 g of p-guanidinobenzoic acid, methyl ester, hydrochloride as white crystals, mp 137°–138.5° C. (dec.).

A 9.15 g amount of the above compound was partially dissolved in 100 ml of methanol (stored over 4A molecular sieves) and 2.15 g of sodium methoxide was added. The mixture was stirred briefly, then 7.0 g of 3-dimethylamino-1-(4-pyridinyl)-2-propen-1-one was added and the mixture was heated under argon with stirring for 21.5 hours. The reaction mixture was cooled in an ice bath, then filtered and washed with cold methanol. The residue was dissolved in a mixture of dichloromethane and methanol and filtered to remove sodium chloride. The filtrate was concentrated on a steam bath until crystal formation. The mixture was allowed to stand at room temperature for 16 hours then was filtered. The precipitate was washed with ice cold methanol then dried and gave 5.8 g of the desired product, mp 194.5°–196.5° C.

EXAMPLE 6

3-Dimethylamino-1-(3-indolyl)-2-propen-1-one

A mixture of 3.18 g of 3-acetylindole and 5.17 ml (4.36 g) of tert-butoxybis(dimethylamino)methane was heated on a steam bath for 4 hours. The cooled reaction mixture was triturated with n-hexanes and gave a semisolid. The solvent was removed in vacuo and the material was triturated with dichloromethane giving 3.08 g of the desired compound as a tan crystalline solid, mp 239°–245° C.,

EXAMPLE 7

3-Dimethylamino-1-(5-methyl-2-thienyl)-2-propen-1-one

A mixture of 56.08 g of 2-acetyl-5-methylthiophene and 250 ml of N,N-dimethylformamide dimethylacetal was heated on a steam bath under an air condenser for 16 hours. The mixture was cooled in an ice bath and filtered giving 66.82 g of the desired compound, mp 118°–121° C.

EXAMPLE 8

3-(Dimethylamino)-1-(5-methyl-2-furanyl)-2-propen-1-one

A mixture of 37.24 g of 2-acetyl-5-methylfuran and 150 ml of N,N-dimethylformamide dimethylacetal was heated on a steam bath under an air condenser for 16.5 hours. The solvent was removed in vacuo and the residue taken up in dichloromethane and passed through a short column of magnesium silicate. The filtrate was evaporated on a steam bath with the addition of n-hexanes to a volume of 100–150 ml. Cooling with scratching gave 28.31 g of the desired compound, mp 123°–125° C.

EXAMPLE 9

3-(Dimethylamino)-1-(1H-pyrrol-2-yl)-(E)-2-propen-1-one

A mixture of 39.6 g of 2-acetylpyrrole and 104 ml (87.7 g) of tert-butoxy bis(dimethylamino)methane was heated on a steam bath for 20 minutes. The reaction was allowed to subside, then heating was continued for 6 hours. The mixture solidified then was slurried in hexane with chilling. The crude product was collected, washed with hexane and dried. The solid was dissolved in chloroform containing 5% methanol and filtered through magnesium silicate. The eluent was evaporated in vacuo and the residue was recrystallized from dichloromethane/hexane containing a small amount of methanol. The solid was collected, washed with hexane then dried in vacuo giving 25.1 g of the desired compound as yellow crystals, mp 192°–193° C. (dec.).

The following 3-(dimethylamino)acrylophenone intermediate compounds listed in Table III were prepared in a similar manner to the procedures described in Examples 6–8 and by those described in U.S. Pat. Nos. 4,281,000, 4,374,988 and in Case No. 29,240, Ser. No. 672,753, filed on Nov. 19, 1984.

TABLE III 3-(Dimethylamino)acrylophenone Intermediates $$R_3-\overset{O}{\overset{\|}{C}}-\overset{R_4}{\overset{|}{C}H_2} + (CH_3)_2-N-\overset{R_5}{\overset{|}{C}}(OCH_3)_2 \longrightarrow$$

$$R_3-\overset{O}{\overset{\|}{C}}-\overset{R_4}{\overset{|}{C}}=\overset{R_5}{\overset{|}{C}}-N(CH_3)_2$$

| Ex. | R₃ | R₄ | R₅ | MP °C. |
|---|---|---|---|---|
| 10 | 2-Furanyl | H | H | 84–86 |
| 11 | 2-pyridinyl | H | H | 127–130 |
| 12 | 2-furanyl | CH₃ | H | Oil |
| 13 | 4-pyridinyl | CH₃ | H | 106–108 |
| 14 | 4-methyl-3- | H | H | 116–118 |

TABLE III-continued 3-(Dimethylamino)acrylophenone Intermediates

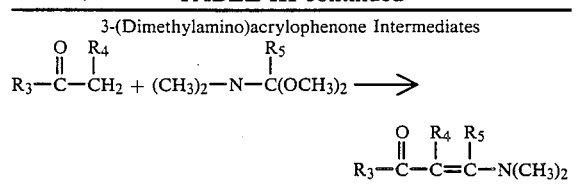

| Ex. | R$_3$ | R$_4$ | R$_5$ | MP °C. |
|---|---|---|---|---|
| 15 | 4-methyl-3-pyridinyl | H | CH$_3$ | 119–120 |
| 16 | 2-pyrazinyl | H | H | 132–133 |
| 17 | 3-thienyl | H | H | 89–90 |
| 18 | 4-quinolinyl | H | H | 45–49 |
| 19 | 3-methyl-2-thienyl | H | H | 45–49 |
| 20 | 1-methyl-1H—pyrrol-2-yl | H | H | 94–95 |
| 21 | 5-methyl-2-thienyl | H | CH$_3$ | 123–126 |
| 22 | 2,5-dimethyl-3-furanyl | H | H | 91–95 |
| 23 | 2-pyridinyl | H | CH$_3$ | 68–70 |
| 24 | 2-thienyl | H | CH$_3$ | 97–99 |
| 25 | 4-pyridinyl | H | CH$_3$ | 88–89 |
| 26 | 3-pyridinyl | H | CH$_3$ | 62–64 |
| 27 | 3-pyridinyl | CH$_3$ | H | 76–78 |
| 28 | 3-methyl-2-pyridinyl | H | H | 97–98 |
| 29 | 2-benzofuranyl | H | H | 137.0–138.5 |
| 30 | 3-pyridinyl | H | H | 97–99 |

TABLE III-continued 3-(Dimethylamino)acrylophenone Intermediates

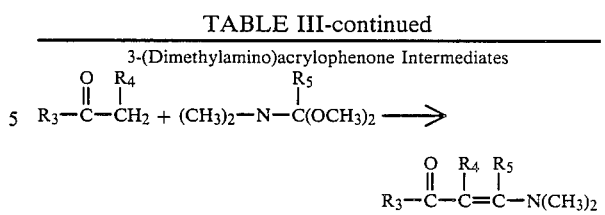

| Ex. | R$_3$ | R$_4$ | R$_5$ | MP °C. |
|---|---|---|---|---|
| 31 | 2-phenothiazine | H | H | |

EXAMPLES 32–251

4,5,6-Substituted-2-pyrimidinamines

The following 4,5,6-substituted-2-pyridinamine final products listed in Table IV were obtained by reacting a 3-(dimethylamino)acrylophenone from Table III and an appropriately substituted phenylguanidine base, carbonate, sulfate, nitrate or hydrochloride salt in an insert solvent such as absolute ethanol, n-propanol, isopropanol, 2-methoxyethanol, or n-butanol and the like, with or without a base such as sodium hydroxide, potassium hydroxide or potassium carbonate and the like by heating at the reflux temperature for from 6–90 hours, then recovering the product in a conventional manner with recrystallization from solvents such as n-propanol, isopropanol, absolute ethanol and the like.

TABLE IV

2-Amino-4,5,6-substituted Pyrimidinamines

| Ex. | Acrylophenone Source | Phenylguanidine Precursor | Product | MP °C. |
|---|---|---|---|---|
| 32 | Ex. 12 | Phenylguanidine carbonate | 4-(2-Furanyl)-5-methyl-N—phenyl-2-pyrimidinamine | 141–142 |
| 33 | Ex. 3 | [3-(Trifluoromethyl)phenyl]guanidine carbonate | 4-(4-Pyridinyl)-N—[3-(trifluoromethyl)phenyl]-2-pyrimidinamine | 198–200 |
| 34 | Ex. 1 | Phenylguanidine carbonate | N—Phenyl-4-(3-pyridinyl)-2-pyrimidinamine | 147–148 |
| 35 | Ex. 1 | (4-Acetylphenyl)guanidine | N—(4-Acetylphenyl)-4-(3-pyridinyl)-2-pyrimidinamine | 181–183 |
| 36 | Ex. 1 | (4-Fluorophenyl)guanidine carbonate | N—(4-Fluorophenyl)-4-(3-pyridinyl)-2-pyrimidinamine | 167–169 |
| 37 | Ex. 11 | (4-Methoxyphenyl)guanidine carbonate | N(4-Methoxyphenyl)-4-(2-pyridinyl)-2-pyrimidinamine | 162–164 |
| 38 | Ex. 3 | (4-Fluorophenyl)guanidine carbonate | N—(4-Fluorophenyl)-4-(4-pyridinyl)-2-pyrimidinamine | 186–188 |
| 39 | Ex. 1 | (4-Bromophenyl)guanidine carbonate | N—(4-Bromophenyl)-4-(3-pyridinyl)-2-pyrimidinamine | 174–175 |
| 40 | Ex. 4 | (4-Fluorophenyl)guanidine carbonate | N—(4-Fluorophenyl)-4-(2-thienyl)-2-pyrimidinamine | 176–178 |
| 41 | Ex. 11 | [3-(Trifluoromethyl)phenyl]guanidine carbonate | 4-(2-Pyridinyl)-N—[3-(trifluoromethyl)phenyl]-2-pyrimidinamine | 161–162 |
| 42 | Ex. 4 | Phenylguanidine carbonate | N—Phenyl-4-(2-thienyl)-2-pyrimidinamine | 137–139 |
| 43 | Ex. 1 | 3-Chloro-4-methylphenylguanidine carbonate | N—(3-Chloro-4-methylphenyl)-4-(3-pyridinyl)-2-pyrimidinamine | 140–145 |
| 44 | Ex. 11 | 3-Methylphenylguanidine carbonate | N—(3-Methylphenyl)-4-(2-pyridinyl)-2-pyrimidinamine | 135–137 |
| 45 | Ex. 3 | 3-Methylphenylguanidine carbonate | N—(3-Methylphenyl)-4-(4-pyridinyl)-2-pyrimidinamine | 157–159 |
| 46 | Ex. 3 | Phenylguanidine carbonate | N—Phenyl-4-(4-pyridinyl)-2-pyrimidinamine | 153–154 |
| 47 | Ex. 1 | 3-Methylphenylguanidine carbonate | N—(3-Methylphenyl)-4-(3-pyridinyl)-2-pyrimidinamine | 102–103 |
| 48 | Ex. 3 | 4-Ethylphenylguanidine carbonate | N—(4-Ethylphenyl)-4-(4-pyridinyl)-2-pyrimidinamine | 138–140 |
| 49 | Ex. 13 | 4-Ethylphenylguanidine carbonate | N—(4-Ethylphenyl)-5-methyl-4-(4-pyridinyl)-2-pyrimidinamine | 132–133 |
| 50 | Ex. 3 | 3,4-Dichlorophenylguanidine carbonate | N—(3,4-Dichlorophenyl)-4-(4-pyridinyl)-2-pyrimidinamine | 214–216 |
| 51 | Ex. 1 | 4-Ethylphenylguanidine carbonate | N—(4-Ethylphenyl)-4-(3-pyridinyl)-2-pyrimidinamine | 120–122.5 |

TABLE IV-continued
2-Amino-4,5,6-substituted Pyrimidinamines

| Ex. | Acrylophenone Source | Phenylguanidine Precursor | Product | MP °C. |
|---|---|---|---|---|
| 52 | Ex. 11 | 4-Ethylphenylguanidine carbonate | N—(4-Ethylphenyl)-4-(2-pyridinyl)-2-pyrimidinamine | 148.5–149.5 |
| 53 | Ex. 4 | 3-Methylphenylguanidine carbonate | N—(3-Methylphenyl)-4-(2-thienyl)-2-pyrimidinamine | 112.5–114.5 |
| 54 | Ex. 10 | Phenylguanidine carbonate | 4-(2-Furanyl)-N—phenyl-2-pyrimidinamine | 144–145 |
| 55 | Ex. 10 | 3-Methylphenylguanidine carbonate | 4-(2-Furanyl)-N—(3-methylphenyl)-2-pyrimidinamine | 98–99.5 |
| 56 | Ex. 14 | 4-Ethylphenylguanidine carbonate | N—(4-Ethylphenyl)-4-(6-methyl-3-pyridinyl)-2-pyrimidinamine | 154–155 |
| 57 | Ex. 15 | 4-Ethylphenylguanidine carbonate | N—(4-Ethylphenyl)-6-methyl-4-(6-methyl-3-pyridinyl)-2-pyrimidinamine | 118–120 |
| 58 | Ex. 16 | 4-Ethylphenylguanidine carbonate | N(4-Ethylphenyl)-4-pyrazinyl-2-pyrimidinamine | 157.5–159 |
| 59 | Ex. 16 | 3-Methylphenylguanidine carbonate | N—(3-Methylphenyl)-4-(4-pyrazinyl)-2-pyrimidinamine | 112.5–117 |
| 60 | Ex. 3 | 2-Methylphenylguanidine carbonate | N—(2-Methylphenyl)-4-pyrazinyl)-2-pyrimidinamine | 129–130.5 |
| 61 | Ex. 3 | 3-Ethylphenylguanidine sulfate | N—(3-Ethylphenyl)-4-(4-pyridinyl)-2-pyrimidinamine | 126–128 |
| 62 | Ex. 3 | 2,5-Dimethylphenylguanidine carbonate | N—(2,5-Dimethylphenyl)-4-(4-pyridinyl-2-pyrimidinamine | 131–134 |
| 63 | Ex. 3 | 2,3-Dimethylhenylguanidine carbonate | N—(2,3-Dimethylphenyl)-4-(4-pyridinyl)-2-pyrimidinamine | 121–123 |
| 64 | Ex. 17 | 3-Methylphenylguanidine carbonate | N—(3-Methylphenyl)-4-(3-thienyl)-2-pyrimidinamine | 104.5–105.5 |
| 65 | Ex. 11 | 2,5-Dimethylphenylguanidine carbonate | N—(2,5-Dimethylphenyl)-4-(2-pyridinyl)-2-pyrimidinamine | 139–142 |
| 66 | Ex. 3 | 3,5-Dimethylphenylguanidine carbonate | N—(3,5-Dimethylphenyl)-4-(4-pyridinyl)-2-pyrimidinamine | 183–185 |
| 67 | Ex. 3 | 1-Naphthylguanidine nitrate | N—1-Naphthalenyl-4-(4-pyridinyl)-2-pyrimidinamine | 174–176 |
| 68 | Ex. 11 | 3,5-Dimethylphenylguanidine hydrochloride | N—(3,5-Dimethylphenyl)-4-(2-pyridinyl)-2-pyrimidinamine | 114–119 |
| 69 | Ex. 11 | 1-Naphthylguanidine nitrate | N—1-Naphthalenyl-4-(2-pyridinyl)-2-pyrimidinamine | 135–138 |
| 70 | Ex. 3 | 2,4-Dimethylphenylguanidine carbonate | N—(2,4-Dimethylphenyl)-4-(4-pyridinyl)-2-pyrimidinamine | 116–118 |
| 71 | Ex. 3 | 2,4,6-Trimethylphenylguanidine carbonate | 4-(4-Pyridinyl)-N—(2,4,6-trimethylphenyl)-2-pyrimidinamine | 142–144 |
| 72 | Ex. 10 | 4-Methoxyphenylguanidine carbonate | 4-(2-Furanyl)-N—(4-methoxyphenyl)-2-pyrimidinamine | 155–158.5 |
| 73 | Ex. 10 | [3-(Trifluoromethyl)phenyl]guanidine carbonate | 4-(2-Furanyl)-N—[3-(trifluoromethyl)phenyl]-2-pyrimidinamine | 150–154 |
| 74 | Ex. 10 | 4-Fluorophenylguanidine carbonate | N—(4-Fluorophenyl)-4-(2-furanyl)-2-pyrimidinamine | 150–152 |
| 75 | Ex. 11 | N—Cyclopentylguanidine sulfate | N—Cyclopentyl-4-(2-pyridinyl)-2-pyrimidinamine | 106–109 |
| 76 | Ex. 11 | 3,4-Dimethylphenylguanidine carbonate | N—(3,4-Dimethylphenyl)-4-(2-pyridinyl)-2-pyrimidinamine | 130–133.5 |
| 77 | Ex. 17 | 4-Methoxyphenylguanidine carbonate | N—(4-Methoxyphenyl)-4-(3-thienyl)-2-pyrimidinamine | 158–160.5 |
| 78 | Ex. 10 | 3-Ethylphenylguanidine sulfate | N—(3-Ethylphenyl)-4-(2-furanyl)-2-pyrimidinamine | 95–98 |
| 79 | Ex. 6 | Phenylguanidine carbonate | 4-(1H—Indol-3-yl)-N—phenyl-2-pyrimidinamine | 188–190 |
| 80 | Ex. 3 | 2-Methoxy-5-methylphenylguanidine carbonate | N—(2-Methoxy-5-methylphenyl)-4-(4-pyridinyl)-2-pyrimidinamine | 96–98.5 |
| 81 | Ex. 20 | 3-Methylphenylguanidine carbonate | N—(3-Methylphenyl)-4-(1-methyl-1H—pyrrol-2-yl)-2-pyrimidinamine | 117–120 |
| 82 | Ex. 20 | 4-Ethylphenylguanidine carbonate | N—(4-Ethylphenyl)-4-(1-methyl-1H—pyrrol-2-yl)-2-pyrimidinamine | 89–91 |
| 83 | Ex. 20 | Phenylguanidine carbonate | 4-(1-Methyl-1H—pyrrol-2-yl)-N—phenyl-2-pyrimidinamine | 118–120 |
| 84 | Ex. 4 | 3-Ethylphenylguanidine sulfate | N—(3-Ethylphenyl)-4-(2-thienyl)-2-pyrimidinamine | 114–116 |
| 85 | Ex. 17 | 3-Ethylphenylguanidine sulfate | N—(3-Ethylphenyl)-4-(3-thienyl)-2-pyrimidinamine | 86–89 |
| 86 | Ex. 6 | 3-Methylphenylguanidine carbonate | 4-(1H—Indol-2-yl)-N—(3-methylphenyl)-2-pyrimidinamine | 164–167 |
| 87 | Ex. 18 | 3-Methylphenylguanidine carbonate | N—(3-Methylphenyl)-4-(4-quinolinyl)-2-pyrimidinamine | 196–198 |
| 88 | Ex. 18 | Phenylguanidine carbonate | N—Phenyl-4-(4-quinolinyl)-2-pyrimidinamine | 182–184 |
| 89 | Ex. 18 | 4-Ethylphenylguanidine carbonate | N—(4-Ethylphenyl)-4-(4-quinolinyl)-2-pyrimidinamine | 176–178 |
| 90 | Ex. 10 | 3,5-Dimethylphenylguanidine | N—(3,5-Dimethylphenyl)-4-(2-fur- | 126–129 |

TABLE IV-continued

2-Amino-4,5,6-substituted Pyrimidinamines

| Ex. | Acrylophenone Source | Phenylguanidine Precursor | Product | MP °C. |
|---|---|---|---|---|
| | | dine hydrochloride | anyl)-2-pyrimidinamine | |
| 91 | Ex. 4 | 3,5-Dimethylphenylguanidine hydrochloride | N—(3,5-Dimethylphenyl)-4-(2-thienyl)-2-pyrimidinamine | 152–155 |
| 92 | Ex. 3 | N—Methyl-N—phenylguanidine hydrochloride | N—Methyl-N—phenyl-4-(4-pyridinyl)-2-pyrimidinamine | 105–107 |
| 93 | Ex. 3 | 2,4-Difluorophenylguanidine hydrochloride | N—(2,4-Difluorophenyl)-4-(4-pyridinyl)-2-pyrimidinamine | 172–174 |
| 94 | Ex. 1 | 2,4-Difluorophenylguanidine hydrochloride | N—(2,4-Difluorophenyl)-4-(3-pyridinyl)-2-pyrimidinamine | 163–165 |
| 95 | Ex. 7 | 3-Methylphenylguanidine carbonate | N—(3-Methylphenyl)-4-(5-methyl-2-thienyl)-2-pyrimidinamine | 114–116 |
| 96 | Ex. 3 | 2,6-Difluorophenylguanidine hydrochloride | N—(2,6-Difluorophenyl)-4-(4-pyridinyl)-2-pyrimidinamine | 174–176 |
| 97 | Ex. 9 | Phenylguanidine carbonate | N—Phenyl-4-(1H—pyrrol-2-yl)-2-pyrimidinamine | 154–157 |
| 98 | Ex. 1 | 4-Tert-butylphenylguanidine sulfate | N—[4-(1,1-Dimethylethyl)phenyl]-4-(3-pyridinyl)-2-pyrimidinamine | 130–133 |
| 99 | Ex. 1 | 2,6-Difluorophenylguanidine hydrochloride | N—(2,6-Difluorophenyl)-4-(3-pyridinyl)-2-pyrimidinamine | 163–166 |
| 100 | Ex. 7 | 3,5-Dimethylhenylguanidine hydrochloride | N—(3,5-Dimethylphenyl)-4-(5-methyl-2-thienyl)-2-pyrimidinamine | 133–135 |
| 101 | Ex. 7 | 4-Ethylphenylguanidine carbonate | N—(4-Ethylphenyl)-4-(5-methyl-2-thienyl)-2-pyrimidinamine | 123–125 |
| 102 | Ex. 11 | 3,4-Dimethylphenylguanidine hydrochloride | N—[(3,4-Dimethylphenyl)methyl]-4-(2-pyridinyl)-2-pyrimidinamine | 158–160 |
| 103 | Ex. 7 | 3,5-Dimethylphenylguanidine hydrochloride | N—(3,5-Dimethylphenyl)-4-(3-methyl-2-thienyl)-2-pyrimidinamine | 151–155 |
| 104 | Ex. 9 | 3-Methylphenylguanidine carbonate | N—(3-Methylphenyl)-4-(1H—pyrrol-2-yl)-2-pyrimidinamine | 129–130 |
| 105 | Ex. 8 | 3-Methylphenylguanidine carbonate | 4-(5-Methyl-2-furanyl)-N—(3-methylphenyl)-2-pyrimidinamine | 119–121 |
| 106 | Ex. 21 | Phenylguanidine carbonate | 4-Methyl-6-(5-methyl-2-thienyl)-N—phenyl-2-pyrimidinamine | 133–135 |
| 107 | Ex. 3 | 4-(Dimethylamino)phenylguanidine dihydrochloride | N—[4-(Dimethylamino)phenyl]-4-(4-pyridinyl)-2-pyrimidinamine | 164–166 |
| 108 | Ex. 3 | 3-Methoxyphenylguanidine hydrochloride | N—(3-Methoxyphenyl)-4-(4-pyridinyl)-2-pyrimidinamine | 159–160 |
| 109 | Ex. 11 | 3-Methoxyphenylguanidine hydrochloride | N—(3-Methoxyphenyl)-4-(2-pyridinyl)-2-pyrimidinamine | 110–113 |
| 110 | Ex. 11 | 4-(Dimethylamino)phenylguanidine dihydrochloride | N—[4-(Dimethylamino)phenyl]-4-(2-pyridinyl)-2-pyrimidinamine | 171–174 |
| 111 | Ex. 1 | 3-Methoxyphenylguanidine hydrochloride | N—(3-Methoxyphenyl)-4-(3-pyridinyl)-2-pyrimidinamine | 126–127 |
| 112 | Ex. 1 | 3,5-Dimethylphenylguanidine hydrochloride | N—(3,5-Dimethylphenyl)-4-(3-pyridinyl)-2-pyrimidinamine | 125–128 |
| 113 | Ex. 1 | 4-(Ethoxycarbonyl)phenylguanidine hydrochloride | 4-[[4-(3-Pyridinyl)-2-pyrimidinyl]amino]benzoic acid, ethyl ester | 197–202 |
| 114 | Ex. 1 | 4-(Dimethylamino)phenylguanidine dihydrochloride | N,N—Dimethyl-N'—[4-(3-pyridinyl)-2-pyrimidinyl]-1,4-benzenediamine | 165–166 |
| 115 | Ex. 22 | Phenylguanidine carbonate | 4-(2,5-Dimethyl-3-furanyl)-N—phenyl-2-pyrimidinamine | 116–118 |
| 116 | Ex. 17 | 4-Ethylphenylguanidine carbonate | N—(4-Ethylphenyl)-4-(3-thienyl)-2-pyrimidinamine | 151–152.5 |
| 117 | Ex. 22 | 3-Methylphenylguanidine carbonate | 4-(2,5-Dimethyl-3-furanyl)-N—(3-methylphenyl)-2-pyrimidinamine | 144–146 |
| 118 | Ex. 22 | 3,5-Dimethylphenylguanidine hydrochloride | 4-(2,5-Dimethyl-3-furanyl)-N—(3,5-dimethylphenyl)-2-pyrimidinamine | 149–152 |
| 119 | Ex. 22 | 4-Ethylphenylguanidine carbonate | 4-(2,5-Dimethyl-3-furanyl)-N—(4-ethylphenyl)-2-pyrimidinamine | 93–96 |
| 120 | Ex. 1 | 3-Dimethylaminophenylguanidine dihydrochloride | N,N—Dimethyl-N'—[4-(3-pyridinyl)-2-pyrimidinyl]-1,3-benzenediamine | 123–125 |
| 121 | Ex. 11 | 3-(Ethoxycarbonyl)phenylguanidine hydrochloride | 3-[[4-(2-Pyridinyl)-2-pyrimidinyl]amino]benzoic acid, ethyl ester | 156–158 |
| 122 | Ex. 11 | 3-(Dimethylamino)phenylguanidine dihydrochloride | N,N—Dimethyl-N'—[4-(2-pyridinyl)-2-pyrimidinyl]-1,3-benzenediamine | 109–111 |
| 123 | Ex. 1 | 3-(Ethoxycarbonyl)phenylguanidine hydrochloride | 3-[[4-(3-Pyridinyl)-2-pyrimidinyl]amino]benzoic acid, ethyl ester | 95–103 |
| 124 | Ex. 10 | 4-(Dimethylamino)phenylguanidine dihydrochloride | N'—[4-(2-Furanyl)-2-pyrimidinyl]-N,N—dimethyl-1,4-benzenediamine | 166–167 |
| 125 | Ex. 4 | 4-(Dimethylamino)phenylguanidine dihydrochloride | N,N—Dimethyl-N'—[4-(2-thienyl)-2-pyrimidinyl]-1,4-benzenediamine | 174–175 |
| 126 | Ex. 22 | 4-(Dimethylamino)phenylguanidine dihydrochloride | N'—[4-(2,5-Dimethyl-3-furanyl)-2-pyrimidinyl]-N,N—dimethyl-1,4-benzenediamine | 126–129 |
| 127 | Ex. 19 | 4-(Dimethylamino)phenylguanidine dihydrochloride | N,N—Dimethyl-N'—[4-(3-methyl-2-thienyl)-2-pyrimidinyl]-1,4-benzenediamine | 145–148 |
| 128 | Ex. 3 | 3-(Dimethylamino)phenylguanidine dihydrochloride | N,N—Dimethyl-N'—[4-(4-pyridinyl)-2-pyrimidinyl]-1,3-benzenediamine | 165–168 |

TABLE IV-continued

2-Amino-4,5,6-substituted Pyrimidinamines

| Ex. | Acrylophenone Source | Phenylguanidine Precursor | Product | MP °C. |
|---|---|---|---|---|
| 129 | Ex. 12 | 3,5-Dimethylphenylguanidine | N—(3,5-Dimethylphenyl)-4-(2-furanyl)-5-methyl-2-pyrimidinamine | 155–158 |
| 130 | Ex. 12 | 4-(Dimethylamino)phenylguanidine dihydrochloride | N'—[4-(2-Furanyl)-5-methyl-2-pyrimidinyl]-N,N—dimethyl-1,4-benzenediamine | 146–148 |
| 131 | Ex. 29 | 4-(Dimethylamino)phenylguanidine dihydrochloride | N'—[4-(2-Benzofuranyl)-2-pyrimidinyl]-N,N—dimethyl-1,4-benzenediamine | 175–178 |
| 132 | Ex. 11 | 2-Guanidinobenzimidazole | N—[4-(2-Pyridinyl)-2-pyrimidinyl]-1H—benzimidazol-2-amine | 276–279.5 |
| 132 | Ex. 23 | Phenylguanidine carbonate | 4-Methyl-N—phenyl-6-(2-pyridinyl)-2-pyrimidinamine | 94–98 |
| 134 | Ex. 4 | 3-(Dimethylamino)phenylguanidine dihydrochloride | N,N—Dimethyl-N'—[4-(2-thienyl)-2-pyrimidinyl]-1,3-benzenediamine | 118–120 |
| 135 | Ex. 8 | 3-(Dimethylamino)phenylquanidine dihydrochloride | N,N—Dimethyl-N'—[4-(5-methyl-2-furanyl)-2-pyrimidinyl]-1,3-benzenediamine | 126–129 |
| 136 | Ex. 22 | 3-(Dimethylamino)phenylguanidine dihydrochloride | N'—[4-(2,5-Dimethyl-3-furanyl)-2-pyrimidinyl]-N,N—dimethyl-1,3-benzenediamine | 153–155 |
| 137 | Ex. 3 | 4-Aminoacetylphenylguanidine hydrochloride | N—[4-[[4-(4-Pyridinyl)-2-pyrimidinyl]amino]phenyl]acetamide | 294–296 |
| 138 | Ex. 3 | 4-(Diethylamino)phenylguanidine dihydrochloride | N,N—Diethyl-N'—[4-(4-pyridinyl)-2-pyrimidinyl]-1,4-benzenediamine | 126–128 |
| 139 | Ex. 1 | 4-(Diethylamino)phenylguanidine dihydrochloride | N,N—Diethyl-N'—[4-(3-pyridinyl)-2-pyrimidinyl]-1,4-benzenediamine | 100–104 |
| 140 | Ex. 17 | Phenylguanidine carbonate | N—Phenyl-4-(3-thienyl)-2-pyrimidinamine | 142–143 |
| 141 | Ex. 11 | 4-Fluorophenylguanidine carbonate | N—(4-Fluorophenyl)-4-(2-pyridinyl)-2-pyrimidinamine | 207–209 |
| 142 | Ex. 11 | 4-Chlorophenylguanidine carbonate | N—(4-Chlorophenyl)-4-(2-pyridinyl)-2-pyrimidinamine | 220–222 |
| 143 | Ex. 3 | 4-Methylphenylguanidine carbonate | N—(4-Methylphenyl)-4-(4-pyridinyl)-2-pyrimidinamine | 197.5–198.5 |
| 144 | Ex. 31 | N—[3-(Trifluoromethyl)-phenyl]guanidine carbonate | 4-(2-Phenothiazine)-N—[3-(trifluoromethyl)phenyl]-2-pyrimidinamine | 240–243 |
| 145 | Ex. 31 | 4-Methoxyphenylguanidine carbonate | N—(4-Methoxyphenyl)-4-(2-phenothiazine)-2-pyrimidinamine | 220–225 |
| 146 | Ex. 31 | 3,4-Dichlorophenylguanidine carbonate | N—(3,4-Dichlorophenyl)-4-(2-phenothiazine)-2-pyrimidinamine | 235–238 |
| 147 | Ex. 11 | 2,4-Dimethylphenylguanidine carbonate | N—(2,4-Dimethylphenyl)-4-(2-pyridinyl)-2-pyrimidinamine | 111.5–113.5 |
| 148 | Ex. 3 | 2-Methoxyphenylguanidine carbonate | N—(2-Methoxyphenyl)-4-(4-pyridinyl)-2-pyrimidinamine | 112–117 |
| 149 | Ex. 3 | 2,5-Dimethoxyphenylguanidine carbonate | N—(2,5-Dimethoxyphenyl)-4-(4-pyridinyl)-2-pyrimidinamine | 151.5–155.0 |
| 150 | Ex. 11 | 2-Methoxy-5-methylphenylguanidine carbonate | N—(2-Methoxy-5-methylphenyl)-4-(2-pyridinyl)-2-pyrimidinamine | 117–118.5 |
| 151 | Ex. 3 | 3,4-Dimethylphenylguanidine hydrochloride | N—[(3,4-Dimethylphenyl)methyl]-4-(4-pyridinyl)-2-pyrimidinamine | 132–136 |
| 152 | Ex. 29 | 3-Methylphenylguanidine carbonate | 4-(2-Benzofuranyl)-N—(3-methylphenyl)-2-pyrimidinamine | 143–144 |
| 153 | Ex. 3 | 3,4-Dimethylphenylguanidine carbonate | N—(3,4-Dimethylphenyl)-4-(4-pyridinyl)-2-pyrimidinamine | 169–171.5 |
| 154 | Ex. 17 | 4-Fluorophenylguanidine carbonate | N—(4-Fluorophenyl)-4-(3-thienyl)-2-pyrimidinamine | 185–187 |
| 155 | Ex. 31 | Phenylguanidine carbonate | 4-(10H—Phenothiazin-2-yl)-N—phenyl-2-pyrimidinamine | 218–220 |
| 156 | Ex. 6 | 4-Ethylphenylguanidine carbonate | N—(4-Ethylphenyl)-4-(1H—indol-3-yl)-2-pyrimidinamine | 209–210 |
| 157 | Ex. 3 | 1,1'-Biphenylguanidine hydrochloride | N—[1,1'—Biphenyl]-4-yl-4-(4-pyridinyl)-2-pyrimidinamine | 203–205 |
| 158 | Ex. 3 | [4-(1,1-Dimethylethyl)-phenyl]guanidine sulfate | N—[4-(1,1-Dimethylethyl)phenyl]-4-(4-pyridinyl)-2-pyrimidinamine | 181–183 |
| 159 | Ex. 11 | N—Methyl-N—phenylguanidine hydrochloride | N—Methyl-N—phenyl-4-(2-pyridinyl)-2-pyrimidinamine | 88–91 |
| 160 | Ex. 9 | 4-Ethylphenylguanidine carbonate | N—(4-Ethylphenyl)-4-(1H—pyrrol-2-yl)-2-pyrimidinamine | 131–133 |
| 161 | Ex. 19 | Phenylguanidine carbonate | 4-(3-Methyl-2-thienyl)-N—phenyl-2-pyrimidinamine | 137–140 |
| 162 | Ex. 25 | 4-Dimethylaminophenylguanidine dihydrochloride | N,N—Dimethyl-N'—[4-methyl-6-(4-pyridinyl)-2-pyrimidinyl]-1,4-benzenediamine | 153–154 |
| 163 | Ex. 26 | 3,5-Dimethylphenylguanidine hydrochloride | N—(3,5-Dimethylphenyl)-4-methyl-6-(3-pyridinyl)-2-pyrimidinamine | 136–140 |
| 164 | Ex. 12 | N—[3-(Trifluoromethyl)-phenyl]guanidine carbonate | 4-(2-Furanyl)-5-methyl-N—[3-(trifluoromethyl)phenyl]-2-pyrimidinamine | 169–171 |

TABLE IV-continued

2-Amino-4,5-substituted Pyrimidinamines

| Ex. | Acrylophenone Source | Phenylguanidine Precursor | Product | MP °C. |
|---|---|---|---|---|
| 165 | Ex. 23 | N—(3,5-Dimethylphenyl)-guanidine | N—(3,5-Dimethylphenyl)-4-methyl-6-(2-pyridinyl)-2-pyrimidinamine | 110–112 |
| 166 | Ex. 10 | 2-Guanidinobenzimidazole | N—[4-(2-Furanyl)-2-pyrimidinyl]-1H—benzimidazol-2-amine | 306.5–308 |
| 167 | Ex. 23 | N—[4-(Dimethylamino)-phenyl]guanidine dihydrochloride | N,N—Dimethyl-N'—[4-methyl-6-(2-pyridinyl)-2-pyrimidinyl]-1,4-benzenediamine | 145–148 |
| 168 | Ex. 3 | 4-(1-Imidazolyl)phenyl-guanidine dihydrochloride | N—[4-(1H—Imidazol-1-yl)phenyl]-4-(4-pyridinyl)-2-pyrimidinamine | >320 |
| 169 | Ex. 30 | 4-(1-Imidazolyl)phenyl-guanidine dihydrochloride | N—[4-(1H—Imidazol-1-yl)phenyl]-4-(3-pyridinyl)-2-pyrimidinamine | 134–174 (Dec.) |
| 170 | Ex. 11 | N—[4-Diethylamino)phenyl]guanidine dihydrochloride | N,N—Diethyl-N'—[4-(2-pyridinyl)-2-pyrimidinyl]-1,4-benzenediamine | 138–139 |
| 171 | Ex. 11 | 4-(1-Imidazolyl)phenyl-guanidine dihydrochloride | N—[4-(1H—Imidazol-1-yl)phenyl]-4-(2-pyridinyl)-2-pyrimidinamine | 204–206 |
| 172 | Ex. 10 | 4-(1-Imidazolyl)phenyl-guanidine dihydrochloride | 4-(2-Furanyl)-N—[4-(1H—imidazol-1-yl)phenyl]-2-pyrimidinamine | 211–212.5 |
| 173 | Ex. 12 | N—[3-Dimethylamino)phenyl]guanidine dihydrochloride | N,N—Dimethyl-N'—[4-(2-furanyl)-5-methyl-2-pyrimidinyl]-1,3-benzenediamine | 154–156 |
| 174 | Ex. 21 | N—[3-Dimethylamino)phenyl]guanidine dihydrochloride | N,N—Dimethyl-N'—[4-(5-methyl-2-thienyl)-2-pyrimidinyl]-1,3-benzenediamine | 130–133 |
| 175 | Ex. 17 | N—[4-(Dimethylamino)-phenyl]guanidine dihydrochloride | N,N—Dimethyl-N'—[4-(3-thienyl)-2-pyrimidinyl]-1,4-benzenediamine | 173–174 |
| 176 | Ex. 13 | N—[3-(Dimethylamino)-phenyl]guanidine dihydrochloride | N,N—Dimethyl-N'—[4-methyl-6-(4-pyridinyl)-2-pyrimidinyl]-1,3-benzenediamine | 200–201 |
| 177 | Ex. 4 | 4-(1-Imidazolyl)phenyl-guanidine hydrochloride | N—[4-(1H—Imidazol-1-yl)phenyl]-4-(2-thienyl)-2-pyrimidinamine | 179–189 (Dec.) |
| 178 | Ex. 19 | N—(3-Methoxyphenyl)-guanidine hydrochloride | N—(3-Methoxyphenyl)-4-(3-methyl-2-thienyl)-2-pyrimidinamine | 120–123 |
| 179 | Ex. 30 | N—[4-(Acetylamino)phenyl]guanidine hydrochloride | N—[4-[[4-(3-Pyridinyl)-2-pyrimidinyl]amino]phenyl]acetamide | 192–195 |
| 180 | Ex. 30 | N—(4-Benzenesulfonamido)-guanidine hydrochloride | 4-[[4-(3-Pyridinyl)-2-pyrimidinyl]amino]benzenesulfonamide | 224–225 |
| 181 | Ex. 3 | N—(3-Chlorophenyl)guanidine carbonate | N—(3-Chlorophenyl)-4-(4-pyridinyl)-2-pyrimidinamine | 160–161 |
| 182 | Ex. 30 | N—(3-Chlorophenyl)guanidine carbonate | N—(3-Chlorophenyl)-4-(3-pyridinyl)-2-pyrimidinamine | 146–148 |
| 183 | Ex. 17 | N—(3-Methoxyphenyl)-quanidine hydrochloride | N—(3-Methoxyphenyl)-4-(3-thienyl)-2-pyrimidinamine | 142–145 |
| 184 | Ex. 4 | N—(3-Methoxyphenyl)-guanidine hydrochloride | N—(3-Methoxyphenyl)-4-(2-thienyl)-2-pyrimidinamine | 151–153 |
| 185 | Ex. 30 | N—Methyl-N—acetyl-phenyl-guanidine hydrochloride | N—Methyl-N—[4-[[4-(3-pyridinyl)-2-pyrimidinyl]amino]phenyl]acetamide | 194–197 |
| 186 | Ex. 3 | N—Methyl-N—acetyl-phenyl-guanidine hydrochloride | N—Methyl-N—[4-[[4-pyridinyl)-2-pyrimidinyl]amino]phenyl]acetamide | 233–234 |
| 187 | Ex. 11 | N—Methyl-N—acetyl-phenyl-guanidine hydrochloride | N—Methyl-N—[4-[[2-pyridinyl)-2-pyrimidinyl]amino]phenyl]acetamide | 179–181 |
| 188 | Ex. 10 | N—(3-Methoxyphenyl)-guanidine hydrochloride | 4-(2-Furanyl)-N—(3-methoxyphenyl)-2-pyrimidinamine | 114–116 |
| 189 | Ex. 29 | N—(3-Methoxyphenyl)-guanidine hydrochloride | 4-(2-Benzofuranyl)-N—(3-methoxyphenyl)-2-pyrimidinamine | 137 |
| 190 | Ex. 9 | N—(Ethylphenyl)guanidine carbonate | N—(4-Ethylphenyl)-4-(1-methyl-1H—pyrrol-2-yl)-2-pyrimidinamine | 89–91 |
| 191 | Ex. 3 | N—Acetylphenylguanidine hydrochloride | N—[4-[[4-(4-Pyridinyl)-2-pyrimidinyl]amino]phenyl]acetamide | 294–296 |
| 192 | Ex. 10 | N,N—Dimethylphenyl-guanidine dihydrochloride | N,N—Dimethyl-N'—[4-(2-furanyl)-5-methyl-2-pyrimidinyl]-1,3-benzenediamine | 154–156 |
| 193 | Ex. 30 | N—Acetylphenylguanidine hydrochloride | N—[4-[[4-(3-Pyridinyl)-2-pyrimidinyl]amino]phenyl]acetamide | 192–195 |
| 194 | Ex. 11 | Sulfonylaminophenyl-guanidine hydrochloride | 4-[[4-(2-Pyridinyl)-2-pyrimidinyl]amino]benzenesulfonamide | 274–277 |
| 195 | Ex. 11 | N—Acetylphenylguanidine hydrochloride | N—[4-[[4-(2-Pyridinyl)-2-pyrimidinyl]amino]phenyl]acetamide | 254–255 |
| 196 | Ex. 4 | 3-Methoxyphenylguanidine hydrochloride | N—(3-Methoxyphenyl)-4-(2-thienyl)-2-pyrimidinamine | 151–153 |
| 197 | Ex. 30 | 4-(4-Methylpiperazin-1-yl)phenylguanidine dihydrochloride | N—[4-(4-Methyl-1-piperazinyl)-phenyl]-4-(3-pyridinyl)-2-pyrimidinamine | 174–175 |
| 198 | Ex. 7 | 3-Methoxyphenylguanidine | N—(3-Methoxyphenyl)-4-(5-methyl-2- | 149–151 |

TABLE IV-continued

2-Amino-4,5,6-substituted Pyrimidinamines

| Ex. | Acrylophenone Source | Phenylguanidine Precursor | Product | MP °C. |
|---|---|---|---|---|
| | | hydrochloride | thienyl)-2-pyrimidinamine | |
| 199 | Ex. 11 | 3-Chlorophenylguanidine hydrochloride | N—(3-Chlorophenyl)-4-(2-pyridinyl)-2-pyrimidinamine | 164–165 |
| 200 | Ex. 10 | 4-(4-Methylpiperazin-1-yl)phenylguanidine dihydrochloride | 4-(2-Furanyl)-N—[4-(4-methyl-1-piperazinyl)phenyl]-2-pyrimidinamine | 193–195 |
| 201 | Ex. 4 | 4-(4-Methylpiperazin-1-yl)phenylguanidine dihydrochloride | N—[4-(4-Methyl-1-piperazinyl)phenyl]-4-(2-thienyl)-2-pyrimidinamine | 215.5–216.5 |
| 202 | Ex. 11 | 4-(4-Methylpiperazin-1-yl)phenylguanidine dihydrochloride | N—[4-(4-Methyl-1-piperazinyl)phenyl]-4-(2-pyridinyl)-2-pyrimidinamine | 192–193 |
| 203 | Ex. 13 | 4-(4-Methylpiperazin-1-yl)phenylguanidine dihydrochloride | N—[4-(4-Methyl-1-piperazinyl)phenyl]-4-(4-pyridinyl)-2-pyrimidinamine | 207–209 |
| 204 | Ex. 22 | 3-Methoxyphenylguanidine hydrochloride | N—(3-Methoxyphenyl)-4-(2,5-dimethyl-3-furanyl)-2-pyrimidinamine | 124–125 |
| 205 | Ex. 13 | 3-Fluorophenylguanidine hydrochloride | N—(3-Fluorophenyl)-4-(4-pyridinyl)-2-pyrimidinamine | 162 |
| 206 | Ex. 30 | 3-Fluorophenylguanidine hydrochloride | N—(3-Fluorophenyl)-4-(3-pyridinyl)-2-pyrimidinamine | 147–150 |
| 207 | Ex. 11 | 3-Fluorophenylguanidine hydrochloride | N—(3-Fluorophenyl)-4-(2-pyridinyl)-2-pyrimidinamine | 162–164 |
| 208 | Ex. 30 | 4-Acetylphenylguanidine | 1-[3-[[4-(3-Pyridinyl)-2-pyrimidinyl]amino]phenyl]ethanone | 166–168 |
| 209 | Ex. 30 | 1-(Methylethyl)phenylguanidine hydrochloride | N—[4-(1-Methylethyl)phenyl]-4-(3-pyridinyl)-2-pyrimidinamine | 124–125 |
| 210 | Ex. 30 | 3-Ethylphenylguanidine hydrochloride | N—(3-Ethylphenyl)-4-(3-pyridinyl)-2-pyrimidinamine | 80–88 |
| 211 | Ex. 11 | 3-Ethylphenylguanidine hydrochloride | N—(3-Ethylphenyl)-4-(2-pyridinyl)-2-pyrimidinamine | 101–104 |
| 212 | Ex. 11 | 3-Benzenesulfonamidoguanidine hydrochloride | 3-[[4-(2-Pyridinyl)-2-pyrimidinyl]amino]benzenesulfonamide | 223–225 |
| 213 | Ex. 30 | 3-Benzenesulfonamidoguanidine hydrochloride | 3-[[4-(3-Pyridinyl)-2-pyrimidinyl]amino]benzenesulfonamide | 278–280 |
| 214 | Ex. 24 | 4-(1,1-Dimethylethyl)-phenylguanidine hydrochloride | N—[4-(1,1-Dimethylethyl)phenyl]-4-(2-thienyl)-2-pyrimidinamine | 150–154 |
| 215 | Ex. 10 | 4-(Diethylamino)phenylguanidine hydrochloride | N,N—Diethyl-N'—[4-(2-furanyl)-2-pyrimidinyl]-1,4-benzenediamine | 132–133 |
| 216 | Ex. 13 | 4-Benzenesulfonamidoguanidine hydrochloride | 3-[[4-(4-Pyridinyl)-2-pyrimidinyl]amino]benzenesulfonamide | 262–264 |
| 217 | Ex. 13 | 4-Acetylaminophenylguanidine hydrochloride | N—[3-[[4-(4-Pyridinyl)-2-pyrimidinyl]amino]phenyl]acetamide | 267–270 |
| 218 | Ex. 30 | 4-Acetylaminophenylguanidine hydrochloride | N—[3-[[-(3-Pyridinyl)-2-pyrimidinyl]amino]phenyl]acetamide | 239–241 |
| 219 | Ex. 11 | 3-Acetylaminophenylguanidine hydrochloride | N—[3-[[4-(2-Pyridinyl)-2-pyrimidinyl]amino]phenyl]acetamide | 190–192 |
| 220 | Ex. 13 | 3-(1H—Imidazol-1-yl)-phenylguanidine dihydrochloride | N—[3-(1H—Imidazol-1-yl)phenyl]-4-(4-pyridinyl)-2-pyrimidinamine | 232–234 |
| 221 | Ex. 13 | 4-Acetylamino-3-methylphenylguanidine hydrochloride | N—[2-Methyl-4-[[(4-pyridinyl)-2-pyrimidinyl]amino]phenyl]acetamide | 230–235 |
| 222 | Ex. 21 | 4-Acetylaminophenylguanidine hydrochloride | N—[4-[[4-(5-Methyl-2-thienyl)-2-pyrimidinyl]amino]phenyl]acetamide | 227–230 |
| 223 | Ex. 30 | 3-[2-(Diethylaminoethoxy)phenyl]guanidine dihydrochloride | N—[3-[2-(Diethylamino)ethoxy]phenyl]-4-(3-pyridinyl)-2-pyrimidinamine | 79–82 |
| 224 | Ex. 30 | 2-Methoxyphenylguanidine carbonate | N—(2-Methoxyphenyl)-4-(3-pyridinyl)-2-pyrimidinamine | 99–101 |
| 225 | Ex. 24 | 4-Acetylaminophenylquanidine hydrochloride | N—[4-[[4-(2-Thienyl)-2-pyrimidinyl]amino]phenyl]acetamide | 201–203 |
| 226 | Ex. 30 | 4-Acetylamino-3-methylphenylguanidine hydrochloride | N—[2-Methyl-4-[4-(3-pyridinyl)-2-pyrimidinyl]phenyl]acetamide | 233–235 |
| 227 | Ex. 29 | 4-Diethylaminophenylguanidine hydrochloride | N'—[4-(2-Benzofuranyl)-2-pyrimidinyl]-N,N—diethyl-1,4-benzenediamine | 134–136 |
| 228 | Ex. 12 | 4-Acetylaminophenylguanidine hydrochloride | N—[4-[[4-(2-Furanyl)-2-pyrimidinyl]amino]phenyl]acetamide | 230–232 |
| 229 | Ex. 13 | 4-(Imidazol-1-yl)-3-(trifluoromethyl)phenylguanidine dihydrochloride | N—[4-(1H—Imidazol-1-yl)-3-(trifluoromethyl)phenyl]-4-(4-pyridinyl)-2-pyrimidinamine | 238–239 |
| 230 | Ex. 11 | 4-Acetylamino-3-methylphenylguanidine hydrochloride | N—[2-Methyl-4-[[4-(2-pyridinyl)-2-pyrimidinyl]amino]phenyl]acetamide | 232–234 |
| 231 | Ex. 24 | 3-(1-Imidazolyl)phenylguanidine dihydrochloride | N—[3-(1H—Imidazol-1-yl)phenyl]-4-(3-pyridinyl)-2-pyrimidinamine | 137–144 |

TABLE IV-continued

2-Amino-4,5,6-substituted Pyrimidinamines

| Ex. | Acrylophenone Source | Phenylguanidine Precursor | Product | MP °C. |
|---|---|---|---|---|
| 232 | Ex. 24 | 3-(1-Imidazolyl)phenyl-guanidine dihydrochloride | N—[3-(1H—Imidazolyl)phenyl]-4-(2-thienyl)-2-pyrimidinamine | 183–184.5 |
| 233 | Ex. 10 | 3-(1-Imidazolyl)phenyl-quanidine dihydrochloride | 4-(2-Furanyl)-N—[3-(1H—imidazol-1-yl)phenyl]-2-pyrimidinamine | 160–168 |
| 234 | Ex. 10 | 3-(Diethylamino)ethoxy-phenylguanidine dihydrochloride | N—[3-[2-(Diethylamino)ethoxy]phenyl]-4-(2-furanyl)-2-pyrimidinamine | |
| 235 | Ex. 10 | 3-Methylphenylguanidine hydrochloride | 4-(2-Furanyl)-N—(3-methylphenyl)-2-pyrimidinamine, hydrochloride | 195–199 |
| 236 | Ex. 11 | 4-(1-Imidazolyl)-3-(trifluoromethyl)phenyl-guanidine dihydrochloride | N—[4-(1H—Imidazol-1-yl)-3-(trifluoromethyl)phenyl]-4-(2-pyridinyl)-2-pyrimidinamine | 216–218 |
| 237 | Ex. 24 | 3-(Diethylamino)ethoxy-phenylguanidine dihydrochloride | N—[3-[2-(Diethylamino)ethoxy]phenyl]-4-(2-thienyl)-2-pyrimidinamine | |
| 238 | Ex. 10 | 4-Benzenesulfonamido-guanidine hydrochloride | 4-[[4-(2-Furanyl)-2-pyrimidinyl]-amino]benzenesulfonamide | 255–257 |
| 239 | Ex. 21 | 4-Benzenesulfonamido-guanidine hydrochloride | 4-[[4-(5-Methyl-2-thienyl)-2-pyrimidinyl]amino]benzenesulfonamide | 241–245 |
| 240 | Ex. 17 | N—Methylacetylamino-phenylguanidine hydrochloride | N—Methyl-N—[4-[[4-(3-thienyl)-2-pyrimidinyl]amino]phenyl]acetamide | 150–153 |
| 241 | Ex. 13 | 3-[4-Methyl-1-piperazinyl]phenylguanidine hydrochloride | N—[3-(4-Methyl-1-piperazinyl)phenyl]-4-(4-pyridinyl)-2-pyrimidinamine | 150–151.5 |
| 242 | Ex. 10 | 3-[4-Methyl-1-piperazinyl]phenylguanidine hydrochloride | 4-(2-Furanyl)-N—[3-(4-methyl-1-piperazinyl)phenyl]-2-pyrimidinamine | 134.5–136 |
| 243 | Ex. 24 | 3-[4-Methyl-1-piperazinyl]phenylguanidine hydrochloride | N—[3-(4-Methyl-1-piperazinyl)phenyl]-4-(2-thienyl)-2-pyrimidinamine | 125–126.5 |
| 244 | Ex. 13 | 2-Dimethylaminophenyl-guanidine dihydrochloride | N,N—Dimethyl-N'—[4-(4-pyridinyl)-2-pyrimidinyl]-1,2-benzenediamine | 114–119 |
| 245 | Ex. 13 | 3-(Diethylamino)ethoxy-phenylguanidine dihydrochloride | N—[3-[2-(Diethylamino)ethoxy]phenyl]-4-(4-pyridinyl)-2-pyrimidinamine | 100–103 |
| 246 | Ex. 24 | 3-(Diethylamino)ethoxy-phenylguanidine dihydrochloride | N—[4-[2-(Diethylamino)ethoxy]phenyl]-4-(2-thienyl)-2-pyrimidinamine | |
| 247 | Ex. 24 | 3-(Dimethylamino)ethoxy-phenylguanidine dihydrochloride | N—[4-[2-(Dimethylamino)ethoxy]phenyl]-4-(2-thienyl)-2-pyrimidinamine | 96–98 |
| 248 | Ex. 17 | 3-(Dimethylamino)ethoxy-phenylguanidine dihydrochloride | N—[4-[2-(Dimethylamino)ethoxy]phenyl]-4-(3-thienyl)-2-pyrimidinamine | 83–85 |
| 249 | Ex. 21 | 4-Diethylaminophenyl-guanidine hydrochloride | N,N—Diethyl-N'—[4-(5-methyl-2-furanyl)-2-pyrimidinyl]-1,4-benzenediamine | 118–119 |
| 250 | Ex. 21 | 3-Methoxyphenylguanidine hydrochloride | N—(3-Methoxyphenyl)-4-(5-methyl-2-furanyl)-2-pyrimidinamine | |
| 251 | Ex. 13 | 3-(1H—Imidazol-1-yl)-phenylguanidine dihydrochloride | N—[3-(1H—Imidazol-1-yl)phenyl]-4--(4-pyridinyl)-2-pyrimidinamine | 232–239 |

EXAMPLE 252

1-[4-[[4-(3-Pyridinyl)-2-pyrimidinyl]amino]phenyl]ethanone, oxime

A 2.03 mg portion of N-(4-acetylphenyl)-4-(3-pyridinyl)-2-pyrimidinamine was mixed with 210 ml of absolute ethanol and 1.26 g of hydroxylamine hydrochloride. An 18.2 ml portion of 1N sodium hydroxide was added, the mixture was heated at reflux for 2 hours and then evaporated to ¼ volume. This was cooled, the solid collected, washed with ethanol and water and dried, giving 1.9 g of the desired product as cream colored crystals, mp 239°–241° C.

EXAMPLE 253

1-[4-[[4-(3-Pyridinyl)-2-pyrimidinyl]amino]phenyl]ethanone, O-methyloxime

The procedure of Example 252 was repeated using methoxyamine hydrochloride, giving 1.78 g of the desired product as yellow crystals, mp 163°–167° C.

EXAMPLE 254

N-[1-[4-[[4-(3-Pyridinyl)-2-pyrimidinyl]amino]phenyl]ethyl]formamide

A mixture of 7.25 g of N-(4-acetylphenyl)-4-(3-pyridinyl)-2-pyrimidinamine, 100 ml of formamide and 31 ml. of 98% formic acid was refluxed with stirring overnight. The solvents were then boiled off for ½ hour, the reaction cooled and poured into one liter of water. This was extracted with 725 ml of chloroform. The chloroform extract was back washed with 150 ml of water, then dried, filtered and evaporated to a foam. The foam was partitioned between chloroform and water. An equal volume of saturated potassium bicarbonate was added. The organic phase was separated, dried, filtered and evaporated to a foam. This foam was chromatographed on silica gel topped with a thin layer of hydrous magnesium silicate and eluted with chloroform (first four fractions), then with 2% methanol in chloroform (last two fractions). The sixth (final) fraction was evaporated and then crystallized from chloroform-hexane, giving 1.05 g of the desired product as cream colored crystals, mp 118°–121° C.

EXAMPLE 255

N-[4-[2-(Dimethylamino)ethoxy]phenyl]-4-(3-pyridinyl)-2-pyrimidinamine

A 1.10 g portion of dry 4-[[4-(3-pyridinyl)-2-pyrimidinyl]amino]phenol was dissolved in 25 ml of dimethylformamide. A 213 mg portion of sodium hydride (50% in oil) was added, the reaction was sealed and stirred for 45 minutes. A 480 mg portion of 2-dimethylaminoethyl chloride in 2 ml of dimethylformamide was added and the sealed mixture was stirred overnight. The solvent was removed at 60° C. and the residue partitioned between 25 ml of water and 50 ml of ethyl acetate. The aqueous phase was extracted twice with ethyl acetate. The organic phases were combined, washed with 1N sodium hydroxide, dried, filtered and evaporated. The residue was taken up in 20 ml of chloroform, boiled down to ⅓ volume and hexane added to turbidity. The mixture was allowed to stand overnight, giving 400 mg of the desired product as beige crystals, mp 108°–110° C.

EXAMPLE 256

N-[4-[3-(Dimethylamino)propoxy]phenyl]-4-(3-pyridinyl)-2-pyrimidinamine

A 5.46 g portion of 4-[[4-(3-pyridinyl)-2-pyrimidinyl]amino]phenol was reacted with 3-dimethylaminopropyl chloride by the procedure of Example 255, giving 2.9 g of the desired product, mp 85°–87° C.

EXAMPLE 257

N-[4-[2-(Diethylamino)ethoxy]phenyl]-4-(4-pyridinyl)-2-pyrimidinamine

The procedure of Example 256 was repeated using 4-[[4-(4-pyridinyl)-2-pyrimidinyl]amino]phenol, giving 300 mg of the desired product as yellow crystals, mp 85°–87° C.

EXAMPLE 258

N-[4-[2-(Diethylamino)ethoxy]phenyl]-4-(3-pyridinyl)-2-pyrimidinamine

The procedured of Example 255 was repeated, using 2-diethylaminoethyl chloride, giving 3.45 g of the desired product as yellow crystals, mp 87°–89° C.

EXAMPLE 259

N-[4-[2-(Dimethylamino)ethoxy]phenyl]-4-(4-pyridinyl)-2-pyrimidinamine

The procedure of Example 255 was repeated using 4-[[4-(4-pyridinyl)-2-pyrimidinyl]amino]phenol, giving 1.6 g of the desired product as yellow crystals, mp 120°–122° C.

EXAMPLE 260

N-[4-[2-(Dimethylamino)ethoxy]phenyl]-N',N'-dimethyl-N-[4-(4-pyridinyl)-2-pyrimidinyl]-1,2-ethanediamine The procedure of Example 259 was repeated. Subsequent crops of crystals gave 0.4 g of the desired product, mp 87°–91° C.

EXAMPLE 261

N-[4-[3-(Dimethylamino)propoxy]phenyl]-4-(4-pyridinyl)-2-pyrimidinamine

A 2.78 g portion of 4-[[4-(4-pyridinyl)-2-pyrimidinyl]amino]phenol and 2.35 g of 3-dimethylaminopropyl chloride were reacted as described in Example 255, giving 850 mg of the desired product, mp 123°–124.5° C.

EXAMPLE 262

[4-[[4-(4-Pyridinyl)-2-pyrimidinyl]amino]phenoxy]acetic acid, ethyl ester

A mixture of 5.58 g of 4-[[4-(4-pyridinyl)-2-pyrimidinyl]amino]phenol was reacted with ethyl bromo acetate as described in Example 255, giving 1.8 g of the desired product as yellow crystals, mp 109°–111° C.

EXAMPLE 263

N-(4-Methoxyphenyl)-N-methyl-4-(3-pyridinyl)-2-pyrimidinamine

A 2.78 g portion of N-(4-methoxyphenyl)-4-(3-pyridinyl)-2-pyrimidinamine was dissolved in 30 ml of dimethylformamide. A 528 mg portion of sodium hydride (50% in oil) was added, the reaction sealed and stirred for 45 minutes. A solution of 1.70 g of methyl iodide in 2 ml of dimethylformamide was added, the sealed mixture was stirred overnight and the solvent removed. The residue was partitioned between water and chloroform. The organic phase was dried, filtered and evaporated. The residue was crystallized from ether-hexane giving 1.4 g of the desired product as yellow crystals, mp 88°–90° C.

EXAMPLE 264

N-(4-Methoxyphenyl)-N-methyl-4-(4-pyridinyl)-2-pyrimidinamine

The procedure of Example 263 was repeated using N-(4-methoxyphenyl)-4-(4-pyridinyl)-2-pyrimidinamine, giving 510 mg of the desired product as yellow crystals, mp 124°–126° C.

EXAMPLE 265

N-[2-(Diethylamino)ethyl]-4-[[4-(3-pyridinyl)-2-pyrimidinyl]amino]benzamide

A 1.55 ml portion of diethylethylenediamine was added to a solution of 0.01 mole of 4-[[4-(3-pyridinyl)-2-pyrimidinyl]amino]benzoic acid chloride in 50 ml of 1,2-dimethoxyethane. A 10 ml portion of triethylamine was added and the mixture was stirred for 2 hours. The solid was collected, washed with water and recrystallized from absolute ethanol, giving 1.22 g of the desired product, mp 148°–150° C.

EXAMPLE 266

N-Methyl-4-[[4-(3-pyridinyl)-2-pyrimidinyl]amino]benzamide

A 5.85 g portion of 4-[[4-(3-pyridinyl)-2-pyrimidinyl]amino]benzoic acid in 30 ml of thionyl chloride was refluxed on a steam bath for one hour, then evaporated to dryness. The residue was boiled with dimethoxyethane, then cooled and the solid recovered and washed with ether, giving 6.90 g of 4-[[4-(3-pyridinyl)-2-pyrimidinyl]amino]benzoic acid chloride.

A 6.03 g portion of the above acid chloride was suspended in 25 ml of ethanol and 10 ml of 25% aqueous methyl amine was added. The resulting solid was collected, taken up in hot 2-methoxyethanol, cooled and the solid collected, giving 3.35 g of the desired product, mp 254°–257° C.

EXAMPLE 267

4-[[4-(3-Pyridinyl)-2-pyrimidinyl]amino]benzoic acid

To a solution of 19.89 g of 4-[[4-(3-pyridinyl)-2-pyrimidinyl]amino]benzoic acid, ethyl ester in 200 ml of 3A ethanol was added 12.5 ml of 10N sodium hydroxide. This mixture was refluxed on a steam bath for 3 hours and then allowed to evaporate. The residue was taken up in water and treated with 10.4 ml of concentrated hydrochloric acid. The resulting solid was collected and dried, giving 18.11 g of the desired product, mp 311°–317° C.

EXAMPLE 268

[4-[[4-(4-Pyridinyl)-2-pyrimidinyl]amino]phenoxy]acetic acid

An 800 mg portion of [4-[[4-(4-pyridinyl)-2-pyrimidinyl]amino]phenoxy]acetic acid, ethyl ester was dissolved in 100 ml of ethanol and 10.7 ml of 1N sodium hydroxide was added. The mixture was stirred for 2 hours, the solvent removed and the residue dissolved in 5 ml of water. The pH was adjusted to 7.0 with 1N hydrochloric acid and the solid collected, washed with water and dried. The solid was recrystallized from dimethylformamideethanol, giving 600 mg of the desired product as yellow crystals, mp 308°–310° C.

EXAMPLE 269

4-[2-[(4-Methoxyphenyl)amino]-4-pyrimidinyl]-1-methylpyridinium iodide

A 2.0 g portion of N-(4-methoxyphenyl)-4-(4-pyridinyl-2-pyrimidinamine was dissolved in 550 ml of absolute ethanol and filtered. To this was added 10 ml of iodomethane. The reaction was heated on a steam bath for 4 hours. Another 10 ml of iodomethane was added and refluxing was continued overnight. The mixture was cooled, the solid collected, washed with ethanol and dried, giving 2.2 g of the desired product as purple crystals, mp 282°–284° C.

EXAMPLE 270

4-[[4-(3-Pyridinyl)-2-pyrimidinyl]amino]phenol

A 25.0 g portion of N-(4-methoxyphenyl)-4-(3-pyridinyl)-2-pyrimidinamine was dissolved in 200 ml of 48% hydrobromic acid and stirred overnight under an argon atmosphere. The mixture was then heated on a steam bath for 7 hours, cooled overnight and evaporated at 60° C. The residue was basified with 200 ml of saturated potassium bicarbonate solution and stirred for 1.5 hours. The solid was collected, washed with water, dried and recrystallized from hot absolute ethanol, giving 19.1 g of the desired product, mp 223°–225° C.

EXAMPLE 271

4-[[4-(4-Pyridinyl)-2-pyrimidinyl]amino]phenol

The procedure of Example 270 was repeated using N-(4-methoxyphenyl)-4-(4-pyridinyl)-2-pyrimidinamine, giving 3.0 g of the desired product as yellow crystals, mp 268°–270° C.

EXAMPLE 272

N-[4-(2-Propenyloxy)phenyl]-4-(3-pyridinyl)-2-pyrimidinamine

A 2.73 g portion of dry 4-[[4-(3-pyridinyl)-2-pyrimidinyl]amino]phenol was dissolved in 50 ml of dry dimethylformamide. A 528 mg portion of sodium hydride (50% in oil) was added, the reaction was sealed and stirred for 45 minutes. A solution of 1.33 g of allyl bromide in 10 ml of dimethylformamide was added, the sealed mixture was stirred overnight and then evaporated at 80° C. The residue was partitioned between water and chloroform. The organic phase was separated, dried and filtered. The filtrate was evaporated and the residue crystallized from chloroform-hexane, giving 1.7 g of the desired product as yellow crystals, mp 105°–108° C.

EXAMPLE 273

N-(4-Ethylphenyl)-4-(4-pyridinyl)-2-pyrimidinamine, pyridine-1-oxide

A mixture of 2.76 g of N-(4-ethylphenyl)-4-(4-pyridinyl)-2-pyrimidinamine and 3.45 g of m-chloroperbenzoic acid in 100 ml of dichloromethane was stirred at room temperature for 20 hours. The mixture was washed three times with an aqueous saturated solution of sodium bicarbonate and a small amount of saturated saline. The organic layer was dried over magnesium sulfate, filtered through diatomaceous earth, then evaporated in vacuo to give a gelatenous solid. The solid was slurried with 50 ml of dichloromethane and filtered. The solid was washed with a small amount of dichloromethane and air dried to give 500 mg of the product. Recrystallization from absolute methanol gave 460 mg of the desired product, mp 223°–225° C.

EXAMPLE 274

N-Phenyl-4-(4-pyridinyl)-2-pyrimidinamine, dihydrochloride

A 2.0 g amount of N-phenyl-4-(4-pyridinyl)-2-pyrimidinamine was dissolved in 70 ml of dichloromethane with warming. The solution was cooled to room temperature, then hydrogen chloride gas was bubbled in to give a brick red precipitate. The mixture became very thick and more dichloromethane was added. The precipitate was collected, air dried, then dried in vacuo and gave 2.63 g of the desired product as red-orange crystals, mp 259°–262° C.

EXAMPLE 275

N-[4-(4-Pyridinyl)-2-pyrimidinyl]-1,4-benzenediamine, hydrochloride

A 2.85 g amount of N-[4-[[4-(4-pyridinyl)-2-pyrimidinyl]amino]phenyl]acetamide was added to a mixture of 10 ml of concentrated hydrochloric acid and 10 ml of water. The reaction mixture was heated at reflux for 90 minutes, then evaporated in vacuo to obtain a solid. The solid was recrystallized from 3A ethanol/water and gave 2.31 g of the desired product as a yellow crystalline solid, mp 292°–295° C.

Additional hydrochloride salts listed in Examples 276 to 287 in Table V were obtained from the corresponding base compound by following procedures similar to those described in Examples 274 and 275 and employing various other solvents such as isopropyl alcohol, ethanol, ether and the like.

TABLE V

| Ex | Compound | MP °C. |
|---|---|---|
| 276 | 4-(3-Pyridinyl)-N—[3-trifluoromethyl)-phenyl]pyrimidinamine, hydrochloride | 220–223 |
| 277 | N,N,—Dimethyl-N'—[4-(3-pyridinyl)-2-pyrimidinyl]-1,4-benzenediamine, trihydrochloride | 239–245 |
| 278 | N—]4-[2-(Diethylamino)ethoxy]phenyl]-4-(3-pyridinyl)-2-pyrimidinamine, hydrochloride | 115–150 (dec) |
| 279 | N,N—Dimethyl-N'—[4-(2-pyridinyl)-2-(pyrimidinyl)]-1,3-benzenediamine, dihydrochloride | 204–213 |
| 280 | N,N—Dimethyl-N'—[4-(2-pyridinyl)-2-pyrimidinyl]-1,3-benzenediamine, trihydrochloride | 202–205 |
| 281 | N,N—Dimethyl-N'—[4-(4-pyridinyl)-2-pyrimidinyl]-1,3-benzenediamine, dihydrochloride | 178–184 |
| 282 | N,N—Dimethyl-N'—[4-(2-pyridinyl)-2-pyrimidinyl]-1,4-benzenediamine, dihydrochloride | 229–234 |
| 283 | N,N—Dimethy-N'—[4-(4-pyridinyl)-2-pyrimidinyl]-1,4-benzenediamine, trihydrochloride | 232–235 |
| 284 | N—[4-(1-Aminoethyl)phenyl]-4-(3-pyridinyl)-2-pyrimidinamine, trihydrochloride | |
| 285 | N—[3-(1H—Imidazol-1-yl)phenyl]-4-(2-pyridinyl)-2-pyrimidinamine, hydrochloride | 232.5–234 |
| 286 | N—[3-(1H—Imidazol-1-yl)phenyl]-4-(4-pyridinyl)-2-pyrimidinamine, hydrochloride | 259–266 |
| 287 | 4-(2-Furanyl)-N—[3-(4-methyl-1-piperazinyl)phenyl]-2-pyrimidinamine, hydrochloride | 259–263 |

EXAMPLE 288

N-Phenyl-4-(4-pyridinyl)-2-pyrimidinamine, sulfate

A 2.48 g amount of N-phenyl-4-(4-pyridinyl)-2-pyrimidinamine was dissolved in 120 ml of absolute ethanol with heating, then a solution of 1.02 g of concentrated sulfuric acid in 25 ml of ethanol was added dropwise with stirring. The mixture turned orange then a yellow precipitate formed. The mixture was chilled, the preciptate was collected, by filtration, washed with cold ethanol then with ether, and air dried to give 2.73 g of yellow-orange crystals.

The preceding compound was dissolved in a small amount of water, then a saturated aqueous solution of sodium bicarbonate was added to pH 8.0 to yield a light yellow precipitate. The precipitate was collected, washed with water and dried in vacuo. A 2.25 g portion this material was recrystallized from about 200 ml of absolute methanol in the cold. The product was collected, washed with absolute ethanol and dried in vacuo to give 1.75 g of the desired product as orange crystals, mp 233°–235° C.

Additional sulfate salts which were prepared from the corresponding base compound in the manner described hereinabove are listed as Examples 289 to 300 in Table VI.

TABLE VI

| Ex | Compound | MP °C. |
|---|---|---|
| 289 | 4-(2-Pyridinyl)-N—[3-trifluoromethyl)-phenyl]-2-pyrimidinamine, sulfate | 208–211 |
| 290 | N—(3-Methylphenyl)-4-(2-thienyl)-2-pyrimidinamine, sulfate | 207.5–210 |
| 291 | 4-(2-Furanyl)-N—(3-methylphenyl)-2-pyrimidinamine sulfate | 187–193 |
| 292 | 4-(4-Pyridinyl)-Nj—[3-(trifluoromethyl)phenyl)]-2-pyrimidinamine, sulfate | 250–253 |
| 293 | N—(4-Methoxyphenyl)-4-(3-pyridinyl)-2-pyrimidinamine, sulfate | 103–123 |
| 294 | N—Phenyl-4-(3-pyridinyl)-2-pyrimidinamine, sulfate | 167–187 |
| 295 | 4-(3-Pyridinyl)-N—[3-trifluoromethyl)phenyl]-2-pyrimidinamine, sulfate | 196–199 |
| 296 | N—(3,5-Dimethylphenyl)-[4-(3-pyridinyl)-2-pyrimidinamine, sulfate | 209–214 |
| 297 | N—(3,5-Dimethylphenyl)-4-(2-pyridinyl)-2-pyrimidinamine, sulfate | 216–218 |
| 298 | N—(3,5-Dimethylphenyl)-4-methyl-6-(5-methyl-2-thienyl)-2-pyrimidinamine, sulfate | 232–234 |
| 299 | 4-(2-Furanyl)-5-methyl-Nj—phenyl-2-pyrimidinamine, sulfate | 140–144 |
| 300 | N,N—Dimethyl-N'—[4-(4-pyridinyl)-2-pyrimidinyl]-1,3-benzenediamine, sulfate | 204–211 |

EXAMPLE 301

N-Phenyl-4-(4-pyridinyl)-2-pyrimidinamine, phosphate

A 2.0 g amount of N-phenyl-4-(4-pyridinyl)-2-pyrimidinamine was dissolved in 100 ml of ethanol with heating. The solution was allowed to cool to room temperature, then a solution of 2.07 g of phosphoric acid in 25 ml of ethanol was added with stirring. The mixture was chilled for several hours, then the precipitate which formed was collected by filtration, washed twice with cold ethanol and dried in vacuo for 16 hours to give 3.43 g of the desired product as orange crystals, mp 210.5°–212.5° C.

Additional phosphate salts which were prepared from the corresponding base compound in the manner described hereinabove are listed as Examples 302 to 305 in Table VII.

TABLE VII

| Ex | Compound | MP °C. |
|---|---|---|
| 302 | N—(3,5-Dimethylphenyl)-4-(3-pyridinyl)-2-pyrimidinamine, phosphate | 190–192 |
| 303 | N—(4-Methoxyphenyl)-4-(3-pyridinyl)-2-pyrimidinamine, phosphate | 185–188 |
| 304 | N—Phenyl-4-(3-pyridinyl)-2-pyrimidinamine phosphate | 176–179 |
| 305 | N—(3,5-Dimethylphenyl)-4-(2-pyridinyl)-2-pyrimidinamine, phosphate | 199–202 |

EXAMPLE 306

N-Phenyl-4-(4-pyridinyl)-2-pyrimidinamine, (Z)-2-butenedioate (1:1)

A mixture of 4.97 g of N-phenyl-4-(4-pyridinyl)-2-pyrimidinamine and 2.55 g of maleic acid was dissolved in hot 2-methoxyethanol. Cooling gave 4.15 g of the desired product as an orange crystalline solid, mp 211°–214° C.

EXAMPLE 307

N-Phenyl-4-(4-pyridinyl)-2-pyrimidinamine, dinitrate

A 2.0 g amount of N-phenyl-4-(4-pyridinyl)-2-pyrimidinamine was dissolved in 100 ml of ethanol with heating. The solution was allowed to cool to room temperature, then a solution of 1.5 ml of concentrated nitric acid in 25 ml of ethanol was added with stirring to give a red-orange precipitate. The mixture was allowed to stand 30 minutes at room temperature, then was chilled for several hours. The solid was collected, washed with cold absolute ethanol and air dried to give 2.80 g of the desired product as red-orange crystals, mp 167°–169° C. (dec.).

EXAMPLE 308

N-Phenyl-4-(4-pyridinyl)-2-pyrimidinamine, compound with 2-hydroxy-1,2,3-propanetricarboxylate (2:1)

A mixture of 4.97 g of N-phenyl-4-(4-pyridinyl)-2-pyrimidinamine and 4.62 g of citric acid was dissolved in hot absolute ethanol. Cooling gave 6.14 g of the product of the example as a yellow cystalline solid, mp 155°–157° C.

EXAMPLE 309

Oxo[phenyl[4-(4-pytridinyl)-2-pyrimidinyl]amino]acetic acid, ethyl ester

A 4.08 g portion of 2-phenylamino-4-(4-pyridinyl)-pyrimidine was dissolved in 20 ml of dimethylformamide. A 5 g portion of 50% sodium hydride in oil was added using 10 ml of dimethylformamide as a wash. When bubbling ceased, a solution of 2.23 ml of ethyl oxalyl chloride in 10 ml of dimethylformamide was added dropwise. Chloroform and aqueous 10% potassium bicarbonate were added. The organic layer was separated, dried, filtered and evaporated giving the desired product.

EXAMPLE 310

N-[4-(2-Pyridinyl)-2-pyrimidinyl]-1,4-benzenediamine, dihydrochloride

A 12.86 g portion of N-[4-[[4-(2-pyridinyl)-2-pyrimidinyl]amino]phenyl]acetamide in a mixture of 40 ml of water and 40 ml of concentrated hydrochloric acid was refluxed for 30 minutes and then cooled. The solid was collected and dried, giving 10.84 g of the desired product, mp 285°–288° C.

Following the procedure of this Example, and using as starting materials the products of the indicated examples, the products of Examples 311–322 in Table VIII were derived.

TABLE VIII

| Ex. | Starting Material | Product | MP °C. |
|---|---|---|---|
| 311 | Ex. 185 | N—Methyl-N'—[4-(3-pyridinyl)-2-pyrimidinyl]-1,4-benzenediamine | 164–166 |
| 312 | Ex. 187 | N—Methyl-N'—[4-(2-pyridinyl)-2-pyrimidinyl]-1,4-benzenediamine | 110–112 |
| 313 | Ex. 218 | N—[4-(3-Pyridinyl)-2-pyrimidinyl]-1,3-benzenediamine, dihydrochloride | 279–284 |
| 314 | Ex. 217 | N—[4-(4-Pyridinyl)-2-pyrimidinyl]-1,3-benzenediamine | 199–202 |
| 315 | Ex. 221 | 2-Methyl-N—[4-(4-pyridinyl)-2-pyrimidinyl]-1,4-benzenediamine, dihydrochloride | 297–304 |
| 316 | Ex. 219 | N—[4-(2-Pyridinyl)-2-pyrimidinyl]-1,3-benzenediamine | 153–156 |
| 317 | Ex. 182 | N—[3-(1-Aminomethyl)phenyl]-4-(3-pyridinyl)-2-pyrimidinamine | 230(dec.) |
| 318 | Ex. 222 | N—[4-(5-Methyl-2-thienyl)-2-pyrimidinyl]1,4-benzenediamine, dihydrochloride | 284–287 |
| 319 | Ex. 228 | N—[4-(2-Furanyl)-2-pyrimidinyl]-1,4-benzenediamine, dihydrochloride | 261–266 |
| 320 | Ex. 226 | 2-Methyl-N—[4-(3-pyridinyl)-2-pyrimidinyl]-1,4-benzenediamine | 176–178 |
| 321 | Ex. 230 | 2-Methyl-N—[4-(2-pyridinyl)-2-pyrimidinyl]-1,4-benzenediamine | 196–198 |
| 322 | Ex. 191 | N—[4-(4-Pyridinyl)-2-pyrimidinyl]-1,4-benzenediamine | 192–193.5 |

EXAMPLE 323

2-[1-[4-[[4-(3-Pyridinyl)-2-pyrimidinyl]amino]phenyl]ethylidene]hydrazinecarboxamide A 2.9 g portion of 1-[3-[[4-(3-pyridinyl)-2-pyrimidinyl]amino]phenyl]ethanone was mixed with 1.23 g of semicarbazide hydrochloride in 200 ml of absolute ethanol and 1.10 ml of 10N sodium hydroxide was added. This mixture was refluxed overnight, then cooled to room temperature and the solid collected and washed with ethanol, water and ethanol. The solid was recrystallized from dimethylsulfoxide/ethanol, giving 2.9 g of the desired product, mp 256°–258° C.

EXAMPLE 324

N-[4-[2-[bis(1-Methylethyl)amino]ethoxy]phenyl]-4-(3-pyridinyl)-2-pyrimidinamine A 2.64 g portion of 4-[[4-(3-pyridinyl)-2-pyrimidinyl]amino]phenol was dissolved in 60 ml of dimethylformamide by warming on a steam bath and then cooled. A 2.0 g portion of diisopropylaminoethyl chloride hydrochloride was added and dissolved with stirring. A 20 ml portion of 5N sodium hydroxide was added dropwise over 5 minutes, then 5 ml of water was added and the mixture was stirred for 20 hours. The mixture was then heated on a steam bath for 30 minutes, allowed to stand 48 hours and then evaporated. The residual gum was purified by flash dry column chromatography on silica gel eluting fractions 1–3 with methanol and fractions 4–6 with 1% methanol in chloroform. Fractions 4–6 were combined and evaporated, giving 500 mg of the desired product.

EXAMPLE 325

α-Methyl-4-[[4-(3-pyridinyl)-2-pyrimidinyl]amino]benzenemethanol

A 1.45 g portion of 1-[3-[[4-(3-pyridinyl)-2-pyrimidinyl]amino]phenyl]ethanone was dissolved with stirring in 220 ml of ethanol. A 125 mg portion of sodium borohydride was added and stirring continued for 3 hours. A 63 mg portion of sodium borohydride was added and stirring continued overnight. A 2 ml portion of glacial acetic acid was added and the mixture evaporated. The solid was triturated with water, dried and recrystallized from 30 ml of ethanol giving 710 mg of the desired product, mp 145°–147° C.

EXAMPLE 326

N-[1-[3-[[4-(3-Pyridinyl)-2-pyrimidinyl]amino]phenyl]ethyl]formamide

A mixture of 2.9 g of 1-[3-[[4-(3-pyridinyl)-2-pyrimidinyl]amino]phenyl]ethanone, 40 ml of formamide and 13 ml of concentrated formic acid was refluxed for 15 hours, then cooled and evaporated. The residue was partitioned between unsaturated aqueous potassium bicarbonate and chloroform. The organic phase was separated, dried, filtered and evaporated. The residue was chormatographed on silica gel, eluting 125 ml fractions, fractions 1-4 with chloroform and fractions 5-7 with 2% methanol in chloroform. Fractions 5-7 were combined and evaporated, giving 1.25 g of the desired product as a yellow foam.

EXAMPLE 327

2-[[4-(3-Pyridinyl)-2-pyrimidinyl]amino]phenol

A mixture of 35 g of N-(2-methoxyphenyl)-4-(3-pyridinyl)-2-pyrimidinamine in 200 ml of 47% aqueous hydrobromic acid was refluxed for 7 hours and then evaporated. The residue was mixed with saturated aqueous potassium bicarbonate and allowed to stand overnight, then filtered. The filtrate was concentrated, giving 3.5 g of the desired compound, mp 166°-169° C.

EXAMPLE 328

N-[3-(1H-Imidazol-1-yl)phenyl]-4-(2-pyridinyl)-2-pyrimidinamine

A solution of 250 ml of 2-acetylpyridine and 500 ml of N,N-dimethylformamide dimethyl acetal was heated on a steam bath for 6 hours. After concentrating the reaction solution under vacuum, 1 liter of hexane was added to the part crystalline residue. The product was collected as small crystalline particles which were washed with an additional liter of hexane. Air drying was followed by drying at 45° C. under vacuum, leaving 350.7 g of 3-dimethylamino-1-(2-pyridinyl)-2-propen-1-one.

A mixture of 289.0 g of imidazole, 292 g of potassium carbonate, 3 liters of dimethyl sulfoxide, and 300.0 g of 1-fluoro-3-nitrobenzene was stirred and heated for 25.5 hours between 105°-110° C. Then the reaction was poured into 6 liters of water and cooled in the refrigerator over the weekend. The crystalline product was collected and washed with 1 liter of water. Air drying gave 357.6 g of solid. The solid was taken up in 2.4 liters of ethyl acetate and the hot solution passed through hydrous magnesium silicate. After boiling the filtrate down to 1.5 liters, it was cooled to give a precipitate which was collected and washed with 200 ml of ethylacetate, to leave 151.7 g of off-white crystals. After evaporating the mother liquor to dryness, the residue was recrystallized from 350 ml of ethyl acetate to give 59.7 g more product. The mother liquor from the second fraction was evaporated and the residual material recrystallized twice from ethyl acetate to give 30.9 g more product. Total product, 242.3 g of 1-(3-nitrophenyl)-1H-imidazole.

In a Parr hydrogenation bottle was placed 75.00 g of 1-(3-nitrophenyl)-1H-imidazole, 0.70 g platinum oxide, and 250 ml of ethanol. Shaking of this mixture in a Parr hydrogenation apparatus was continued until no more hydrogen was taken up. This process was repeated with 76.33 g of the imidazole, 1.0 g of platinum oxide and 250 ml of ethanol and again with 90.4 g of the imidazole, 1.0 g of platinum oxide and 240 ml of ethanol, until a total of 241.63 g had been reduced. For each batch the catalyst was filtered off and the solvent was removed under vacuum; and then the residues were combined to give 207.2 g of gray crystalline amine. Next the amine was recrystallized from 530 ml of 2-propanol. After collecting the product, it was washed with 200 ml of 2-propanol, and dried, under vacuum, to give 156.4 g of 3-(1H-imidazol-1-yl)benzamine.

A solution of 43.3 g of hydrogen chloride in 290 ml of ethanol was added to 189.0 g of 3-(1H-imidazol-1-yl)benzamine in a 2 liter Erlenmeyer flask. Then 104.7 g of cyanamid was added. The mixture was cautiously warmed in a water bath to an internal temperature of 83° C. over 25 minutes. When no exotherm had been noted, the flask was placed inside the steam bath and heated for 2 hours. A final temperature of 97° C. was achieved. The resulting brown syrup which was [3-(1H-imidazol-1-yl)phenyl]guanidine, monohydrochloride, was used in the next reaction without further purification.

A mixture of 164 g of ppotassium carbonate, 209.1 g of 3-dimethylamino-1-(2-pyridyl)-2-propen-1-one, 1.187 mole of crude [3-(1H-imidazol-1-yl)phenyl]guanidine monohydrochloride, and 1 liter of methoxyethanol was stirred and heated under very gentle reflux. A dry-ice condenser filled with water was used to prevent plugging by the dimethylammonium carbonate which is given off by the reaction. The reaction was stopped after 26.5 hours and permitted to stand overnight. A heavy precipitate had formed which was collected as A and washed with 100 ml of ether. The filtrate was concentrated under vacuum as B. Both A and B were triturated with 1.5 liters of water. Then A was washed with 300-400 ml of ethanol, followed by 100 ml of ether to leave, on drying, 172.9 g of gray solid, mp 200°-202° C. Recrystallization of B from 150 ml of 2-propanol gave a black solid, C. Next, a classical fractional recrystallization was carried out using methoxyethanol as the solvent. In the final stages, a large amount of charcoal was added to remove color. In this fashion two main fractions were obtained D, 79.0 g of yellow crystals, mp 204.5°-205.5° C., and E, 18.05 g of yellow crystals, mp 204°-204.5° C. The yield of D plus E was 26% of the desired product.

EXAMPLE 329

1-(2-Chloroethoxy)-3-nitrobenzene

A mixture of 6.96 g. of m-nitrophenol, 100 ml. of 2-butanone, 6.9 g. of potassium carbonate, and 11.74 g. of 2 chloroethyl-tosylate was stirred and heated under reflux for 24 hours. After cooling to room temperature, the salts were filtered off and the filtrate concentrated under vacuum. The residue crystallized on seeding and was recrystallized from carbon tetrachloride to give 8.3 g. of product, m.p. 54.5°-57° C.

EXAMPLE 330

1-[2-(3-Nitrophenoxy)ethyl]-1H-imidazole

After dissolving 3.74 g. of imidazole in 60 ml. of dry N,N-dimethylformamide, 1.78 g. of 50% sodium hydride in oil was added. When the effervescence had stopped (circa 1 hr.), 7.35 g. of 1-(2-chloroethoxy)-3-nitrobenzene was added. After stirring overnight, the reaction was concentrated under vacuum. Water was added to the residue and the product was extracted into chloroform. The product was extracted out of the chloroform layer with dilute hydrochloric acid. Next, the aqueous acid layer was neutralized with potassium carbonate and the oily product extracted into chloroform. Upon drying the chloroform extract with sodium sulfate, it was concentrated under vacuum to an oil which crystallized on standing. Recrystallization from isopropyl acetate gave 6.12 g. of product as the monohydrate, m.p. 52.5°-55.5° C.

EXAMPLE 331

3-[2-(1H-Imidazol-1-yl)ethoxy]benzamine

Using a Parr hydrogenator, 5.00 g. of 1-[2-(3-nitrophenoxy)ethyl]-1H-imidozole in 100 ml. of ethanol and 0.2 g. of platinum oxide was hydrogenated until the hydrogen uptake stopped. The catalyst was filtered off and the filtrate concentrated under vacuum. Several recrystallizations from isopropyl acetate gave 2.8 g. of amine, m.p. 74°-76.5° C.

EXAMPLE 332

[3-[2-(1H-Imidazol-1-yl)ethoxy]phenyl]-guanidine Dihydrochloride

To a solution of 1.7 g. of hydrogen chloride in 50 ml. of ethanol was added 4.70 g. of 3-[2-(1H-imidazol-1-yl)ethoxy]benzamine in 10 ml. of ethanol. After concentration under vacuum a foam was obtained which gradually crystallized. Next 1.95 g. of cyanamid and 20 ml. of ethanol were added and the mixture heated cautiously, first in a water bath, then directly in a steam bath for a total of 5 hours. A light brown oily guanidine resulted, which was used without purification.

EXAMPLE 333

3-[2-(4-Morpholinyl)ethoxy]-benzenamine

N-[2-Chloroethyl)morpholine hydrochloride, 80 g., was partitioned between 5N sodium hydroxide and methylene chloride. After drying the organic layer over magnesium sulfate, the solvent was removed under reduced pressure to leave 65 g. of free amine.

To 36.01 g. of m-aminophenol dissolved in 325 ml. of N,N-dimethylformamide, 16.3 g. of 50% sodium hydride in oil was added. The reaction was stirred for 1 hour, until the effervescence stopped; then 57 g. of N-(2-chloroethyl)morpholine, from above, was added. After stirring overnight, the mixture was heated on a steam bath for ½ hr., then concentrated under vacuum. The residue was taken up in 300 ml. of 2N hydrochloric acid and washed twice with ether. After basifying with 10N sodium hydroxide, the product was extracted into ether, dried (magnesium sulfate), filtered through hydrous magnesium silicate and evaporated to a brown oil. Distillation gave 34.0 g. of a golden oil, b.p. 165°-180° C./0.45 mm.

EXAMPLE 334

[3-[2-(4-Morpholinyl)ethoxy]phenyl]guanidine monohydrochloride

Prepared from 3-[2-(4-morpholinyl)ethoxy]-benzamine by the method of Example 332

EXAMPLE 335

1-(Bromoacetyl)-4-methylpiperazine monohydrochloride

A solution of 10.0 g. of 1-methyepiperazine in 150 ml of chloroform was cooled in a water bath while 17.3 g. of bromoacetyl chloride in 150 ml. of chloroform was added dropwise, with stirring, over ½ hour. A calcium chloride tube protected the reaction from moisture. After stirring overnight, the precipitate was collected and washed with chloroform. The crude product was dried under vacuum at 50° and used as such.

EXAMPLE 336

1-[(4-Aminophenoxy)acetyl]-4-methylpiperazine

Prepared from p-aminophenol and 1-(bromoacetyl)-4-methylpiperazine by the method of Example 333 to give a product of m.p. 71°-73° C.

EXAMPLE 337

1-[[4-[(Aminoiminomethyl)amino]phenoxy]acetyl]-4-methylpiperazine Dihydrochloride Prepared from 1-[(4-aminophenoxy)acetyl]-4-methylpiperazine by the method of Example 332.

TABLE IX

| Ex. | Acryloyl Source | Phenylguanidine precurser | Product | MP °C. |
|---|---|---|---|---|
| 338 | Ex. 11 | [3-[2-(1H-Imidazol-1-yl)-ethoxy]-phenyl]guanidine dihydrochloride | N—[3-[2-(1H--Imidazol-1-yl)-ethoxy]phenyl--4-(2-pyridinyl)-2-pyrimidinamine | 149–151.5 |
| 339 | Ex. 13 | [3-[-(4-morpholinyl)-ethoxy]-phenyl]guanidine monohydrochloride | N—[3-[2-(4-morpholinyl)-ethoxy]phenyl]--4-(4-pyridinyl)-2-pyrimidinamine | 179–181 |
| 340 | Ex. 24 | [3-[2-(4-morpholinyl)ethoxy]-phenyl]guanidine monohydrochloride | N—[3-[2-(4-morpholinyl)ethoxy]-phenyl]-4-(2-thienyl)-2-pyrimidinamine | 134–136 |
| 341 | Ex. 10 | [3-[2-(4-morpholinyl)ethoxy]-phenyl]guanidine monohydrochloride | 4-(2-furanyl)-N—[3-[2-(4-morpholinyl)ethoxy]-phenyl]-2-pyrimidinamine | 88–90 |
| 342 | Ex. 24 | 1-[[4-[(Aminoiminomethyl)amino]-phenoxy]acetyl]-4-methyl piperazine dihydrochloride | 1-Methyl-4-[[4--(2-thienyl)-2-pyrimidinyl]-phenoxy]acetyl)-piperazine | 173–175 |
| 343 | Ex. 24 | (4-chlorophenyl) guanidine carbonate | N—(4-chlorophenyl)-4-(2-thienyl)-2-pyrimidinamine | 185–186 |
| 344 | Ex. 26 | [2-[bis(1-methylethyl)amino[ethoxy [guanidine hydrochloride | N—[2-[2-[bis(1--methylethyl) amino]ethoxy] phenyl]-4-(3-pyridinyl)-2-pyrimidinamine | 54–57 |

The disease diabetes mellitus is characterized by metabolic defects in the production and utilization of glucose which results in the failure to maintain appropriate blood sugar levels. The result of this defect is elevated blood glucose or hyperglycemia. Research on the treatment of diabetes has centered on attempts to normalize fasting and postprandial blood glucose levels. Treatments have included parenteral administration of exogenous insulin, oral administration of drugs and dietary therapies.

Two major forms of diabetes mellitus are now recognized. Type I diabetes, or insulin-dependent diabetes, is a result of an absolute deficiency of insulin, the hormone which regulates glucose utilization. Type II diabetes, or insulin-independent diabetes, often occurs in the face of normal, or even elevated, levels of insulin and appears to be the result of the inability of tissues to respond appropriately to insulin.

The compounds of the present invention and the pharmacologically active acid-addition salts thereof, effectively lower blood glucose levels when administered orally to genetic strains of hyperglycemic mice which are animal models of type II diabetes. The exact mechanism by which they act is not known and the invention should not be construed as limited to any particular mechanism of action. As effective hypoglycemic agents, these compounds are useful for the treatment of hyperglycemia in type II diabetes.

The compounds of this invention were tested for hypoglycemic activity according to the following procedure.

Obese mice [C57 B1/6J (ob/ob)], their lean littermates (ob/± or +/+) and diabetic mice [C57 B1/Ks (db/db)] and their non-diabetic littermates (db/+ or +/+) were obtained from Jackson Laboratories, Bar Harbor, Maine. Obese mice were 8 weeks of age and diabetic mice were 9 weeks of age at the start of the test.

The test compounds were dissolved in methanol, mixed with powdered Purina rodent chow on a weight of compound to weight of chow basis and thoroughly dried.

Groups of 4 control mice received vehicle (methanol) treated chow.

Groups of 4 test mice were fed ad libitum for one month and food consumption was measured daily (on week days) by weighing the food bins before and after the addition of fresh chow. Thus a 40 g mouse fed the test compound at a concentration of 0.02% of the diet would receive a dose of 20 mg/kg/day if it ate 4 g of chow per day.

Blood samples were collected before the first treatment and once at the end of each week of treatment by retro-orbital puncture using the end of each week of treatment by retro-orbital puncture using heparinized capillary tubes. Plasma was separated by centrifugation in a Beckman microfuge for 5 minutes. Plasma glucose concentrations were determined with the Beckman Glucose Analyzer which uses a glucose oxidase method.

The results of this test on representative compounds of this invention appear in Table X.

TABLE X

Effect of Test Compounds on Blood Glucose

| COMPOUND | Type of Mice | Dose % (W/W) | Blood Glucose Levels in mg/100 ml Days | | | | | |
|---|---|---|---|---|---|---|---|---|
| | | | 0 | 5 | 7 | 14 | 21 | 28 |
| N—(4-methylphenyl)-4-(4- | ob/ob | 0.1 | 219 | 137 | | | | |
| pyridinyl)-2-pyrimidinamine | ob/ob | 0.1 | 210 | | 118 | 80 | | |
| | ob/ob | 0.025 | 209 | | 223 | 166 | | |
| N—(4-Chlorophenyl)-4-(2- | ob/ob | 0.1 | 212 | 160 | | | | |
| thienyl)-2-pyrimidinanine | ob/ob | 0.025 | 220 | | 148 | 134 | | |
| N—(4-ethylphenyl)-4-(4- | ob/ob | 0.1 | 216 | 181 | | | | |
| pyridinyl)-2-pyrimidinamine | ob/ob | 0.1 | 223 | 164 | | | | |
| 4-(2-furanyl)-N'phenyl-2-pyrimidinamine | ob/ob | 0.1 | 214 | 166 | | | | |
| N—[4-(1,1-Dimethylethyl) | ob/ob | 0.1 | 208 | 114 | 175 | | | |
| phenyl]-4-(4-pyridinyl)-2- | ob/ob | 0.1 | 214 | 169 | 155 | | | |
| pyrimidinamine | ob/ob | 0.1 | 218 | 124 | | | | |
| | ob/ob | 0.1 | 229 | 118 | | | | |
| | ob/ob | 0.1 | 225 | | 120 | 116 | 131 | 135 |
| | ob/ob | 0.05 | 214 | | 139 | 143 | 180 | 188 |
| | ob/ob | 0.01 | 214 | | 163 | 138 | 181 | 162 |
| | db/db | 0.1 | 426 | | 390 | 174 | 281 | 207 |
| | db/db | 0.05 | 429 | | 314 | 293 | 250 | 270 |
| | db/db | 0.01 | 431 | | 335 | 407 | 400 | 499 |
| N—[4-(Dimethylamino)phenyl] | ob/ob | 0.1 | 240 | 138 | | | | |
| -4-(4-pyridinyl)-2- | ob/ob | 0.1 | 230 | 147 | | | | |
| pyrimidinamine | | | | | | | | |
| N—[4-[3-Dimethylamino)propoxy] phenyl]-4-(3-pyridinyl) -2-pyrimidinamine | ob/ob | 0.1 | 215 | 234 | | | | |
| N—[4-[2-(Diethylamino)ethoxy] phenyl]-4-(3-pyridinyl)-2- pyrimidinamine | ob/ob | 0.1 | 220 | 191 | | | | |
| N'—[4-(2-Benzofurnayl)-2- | ob/ob | 0.1 | 229 | 153 | | | | |
| pyrimidinyl)-N,N—dimethyl- | ob/ob | 0.1 | 202 | 147 | | | | |
| 1,4-benzenediamine | ob/ob | 0.1 | 223 | 144 | | | | |
| N—[4-[2-(Dimethylam- | ob/ob | 0.1 | 218 | 151 | 167 | | | |
| ino)ethoxy]phenyl]-4- | ob/ob | 0.1 | 228 | 144 | | | | |
| (4-pyridinyl)-2- | ob/ob | 0.1 | 225 | 134 | | | | |
| pyrimidinamine | ob/ob | 0.1 | 232 | | 148 | 128 | 155 | 140 |
| | ob/ob | 0.05 | 230 | | 158 | 198 | 196 | 163 |
| | ob/ob | 0.01 | 236 | | 163 | 252 | 175 | 177 |
| | db/db | 0.1 | 369 | | 410 | 403 | 328 | 222 |
| | db/db | 0.05 | 400 | | 277 | 404 | 329 | 250 |
| | db/db | 0.01 | 368 | | 393 | 321 | 494 | 336 |
| N—[4-(1H—Imidazol-1- | db/db | 0.1 | 424 | | 397 | 233 | | |
| yl)phenyl]4-(4-pyri- | ob/ob | 0.1 | 219 | 128 | | | | |
| dinyl)-2-pyrimidin- | ob/ob | 0.025 | 210 | | 200 | 148 | | |
| amine | ob/ob | 0.1 | 211 | | 105 | 140 | | |
| | ob/ob | 0.1 | 222 | | 119 | 132 | | |
| | ob/ob | 0.01 | 219 | | 158 | 159 | | |
| | ob/ob | 0.025 | 222 | | 157 | 175 | | |
| N,N—Diethyl-N¹—[4- | ob/ob | 0.1 | 223 | 138 | | | | |
| (3-pyridinyl)-2-pyrim- | ob/ob | 0.1 | 210 | 163 | | | | |
| idinyl]-1,4-benzene- | ob/ob | 0.1 | 216 | 153 | | | | |

TABLE X-continued

Effect of Test Compounds on Blood Glucose

| COMPOUND | Type of Mice | Dose % (W/W) | \multicolumn{6}{c}{Blood Glucose Levels in mg/100 ml Days} |
|---|---|---|---|---|---|---|---|---|
| | | | 0 | 5 | 7 | 14 | 21 | 28 |
| diamine | | | | | | | | |
| N—[4-(1H—Imidazol- | ob/ob | 0.1 | 225 | 128 | | | | |
| 1-yl)phenyl]-4-(3- | ob/ob | 0.025 | 208 | | 159 | 171 | | |
| pyridinyl)-2-pyrim- | ob/ob | 0.1 | 218 | | 127 | 131 | | |
| idinamine | | | | | | | | |
| N—[4-(1H—Imidazol- | ob/ob | 0.1 | 217 | 171 | | | | |
| 1-yl)phenyl]-4-(2- | ob/ob | 0.1 | 223 | 167 | | | | |
| pyridinyl)-2-pyrimid- | ob/ob | 0.1 | 234 | 141 | | | | |
| inamine | | | | | | | | |
| 4-(2-Furnayl)-N—[4- | ob/ob | 0.1 | 227 | 137 | | | | |
| (1H—imidazol-1-yl) | ob/ob | 0.025 | 215 | | 164 | 244 | | |
| phenyl]-2-pyrimidin- | ob/ob | 0.1 | 214 | | 140 | 160 | | |
| amine | | | | | | | | |
| N—[4-(1H—Imidazol- | ob/ob | 0.1 | 221 | | 109 | 116 | | |
| 1-yl)phenyl]-4-(2- | ob/ob | 0.025 | 221 | | 147 | 171 | | |
| thienyl)-2-pyrimid- | ob/ob | 0.01 | 217 | | 212 | 161 | | |
| inamine | ob/ob | 0.1 | 224 | 125 | | | | |
| | ob/ob | 0.1 | 203 | 131 | | | | |
| | ob/ob | 0.1 | 231 | 126 | | | | |
| | ob/ob | 0.1 | 218 | 134 | | | | |
| | ob/ob | 0.025 | 218 | | 175 | 185 | | |
| | ob/ob | 0.1 | 220 | | 135 | 117 | | |
| | db/db | 0.1 | 423 | | 492 | 349 | | |
| 4-[[4-(3-Pyridinyl)- | ob/ob | 0.1 | 219 | 122 | | | | |
| 2-pyrimidinyl]amino] | ob/ob | 0.1 | 240 | 147 | | | | |
| benzenesulfonamide | ob/ob | 0.1 | 216 | 185 | | | | |
| | ob/ob | 0.1 | 229 | 142 | | | | |
| | ob/ob | 0.1 | 228 | 211 | | | | |
| N—(3-Chlorophenyl)-4 | ob/ob | 0.1 | 220 | 127 | | | | |
| -(4-pyridinyl)-2- | ob/ob | 0.1 | 237 | 163 | | | | |
| pyrimidinamine | ob/ob | 0.1 | 216 | 135 | | | | |
| | ob/ob | 0.1 | 205 | 157 | | | | |
| | ob/ob | 0.025 | 210 | | 157 | 135 | | |
| | ob/ob | 0.1 | 212 | | 173 | 129 | | |
| N—(3-Chlorophenyl)- | ob/ob | 0.1 | 205 | 135 | | | | |
| -4-(3-pyridinyl)-2- | ob/ob | 0.025 | 221 | | 205 | 131 | | |
| pyrimidinamine | ob/ob | 0.1 | 244 | | 211 | 138 | | |
| N—[4-(4-Methyl-1-piperazinyl)phenyl]-4-(3-pyridinyl)-2-pyrimidinamine | ob/ob | 0.1 | 212 | 236 | | | | |
| N—(3-Chlorophenyl)-4-(2-pyridinyl)-2-pyrimidinamine | ob/ob | 0.1 | 207 | 204 | | | | |
| 4-(2-Furnayl)-N—[4- | ob/ob | 0.1 | 203 | 149 | | | | |
| (4-methyl-1-piper- | ob/ob | 0.025 | 210 | | 179 | 130 | | |
| azinyl)phenyl]-2-pyrimidinamine | ob/ob | 0.1 | 229 | | 163 | 141 | | |
| 4-(2-Furanyl)-N— | ob/ob | 0.1 | 221 | 132 | | | | |
| (3-methoxyphenyl) | ob/ob | 0.1 | 239 | 113 | | | | |
| -2-pyrimidinamine | ob/ob | 0.1 | 217 | 162 | | | | |
| | ob/ob | 0.1 | 219 | 209 | | | | |
| N—[4-(4-Methyl-1-piperazinyl)phenyl]-4-(2-thienyl)-2-pyrimidinamine | ob/ob | 0.1 | 203 | 188 | | | | |
| N—[4-(4-Methyl-1-piperazinyl)phenyl]-4-(2-pyridinyl)-2-pyrimidinamine | ob/ob | 0.1 | 204 | 210 | | | | |
| N—[4-(4-Methyl- | ob/ob | 0.1 | 204 | | 118 | 124 | 178 | 161 |
| 1-piperazinyl)phenyl] | ob/ob | 0.025 | 210 | | 157 | 200 | 152 | 202 |
| -4-(4-pyridinyl)-2- | ob/ob | 0.01 | 210 | | 130 | 192 | 178 | 147 |
| pyrimidinamine | db/db | 0.1 | 406 | | 273 | 140 | 178 | 279 |
| | ob/ob | 0.1 | 221 | 125 | | | | |
| | ob/ob | 0.1 | 233 | 131 | | | | |
| | ob/ob | 0.1 | 226 | 117 | | | | |
| | ob/ob | 0.1 | 215 | 138 | | | | |
| | ob/ob | 0.025 | 231 | | 154 | 134 | | |
| | ob/ob | 0.1 | 223 | | 171 | 137 | | |
| N—[3-(1H—Imidazol-1-yl)phenyl]-4-(3-pyridinyl)-2-pyrimidinamine | ob/ob | 0.1 | 225 | 173 | | | | |
| N—[4-[2-(Diethylamino) | ob/ob | 0.1 | 228 | 154 | | | | |
| ethoxy]phenyl]-4-(2-thienyl)-2-pyrimidinamine | ob/ob | 0.1 | 215 | 137 | | | | |

TABLE X-continued

| | Effect of Test Compounds on Blood Glucose | | | | | | | |
|---|---|---|---|---|---|---|---|---|
| | Type of | Dose % | Blood Glucose Levels in mg/100 ml Days | | | | | |
| COMPOUND | Mice | (W/W) | 0 | 5 | 7 | 14 | 21 | 28 |
| N—[2-[2-[Bis(1-methyl-ethyl)amino]ethoxy]phenyl]-4-(3-inamine | ob/ob | 0.1 | 228 | 153 | | | | |

We claim:

1. A method of treating asthma and allergic diseases in a mammal which comprises administering to said mammal an effective amount of a compound selected from the group consisting of those of the formula:

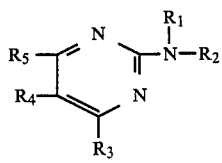

wherein $R_1$ is hydrogen, alkyl($C_1$-$C_3$), —COCO$_2$C$_2$H$_5$ or N, N-dimethylaminoethyl; $R_2$ is mono- or poly-substituted phenyl wherein the substituents are alkyl($C_1$-$C_6$), alkoxy($C_1$-$C_3$), chloro, bromo, monoalkyl($C_1$-$C_3$)amino, dialkyl($C_1$-$C_3$)amino, alkyl($C_1$-$C_3$)keto, propenyloxy, carboxyl, oxyacetic acid, oxyacetic acid ethyl ester, sulfanilamido, N,N-dialkyl($C_1$-$C_3$)sulfanilamido, N-methylpiperazinyl, piperidinyl, 1H-imidazol-1-yl, 1H-triazol-1-yl, 1H-benzimidazol-2-yl, 1-naphthyl, cyclopentyl, 3,4-dimethylbenzyl or moieties of the formulae:

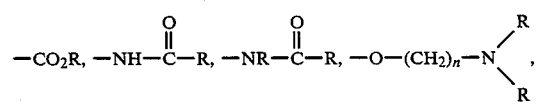

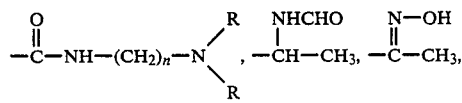

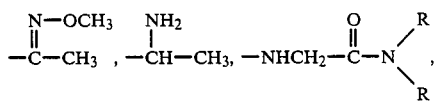

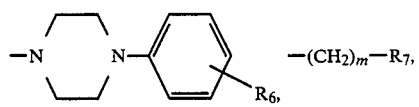

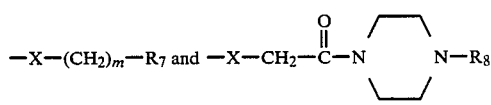

wherein R is alkyl($C_1$-$C_3$), X is oxygen(—O—) or sulfur(—S—), m is 1-3, n is 2 or 3, $R_6$ is hydrogen, alkyl($C_1$-$C_3$), alkoxy($C_1$-$C_3$), chloro, bromo, iodo or trifluoromethyl, $R_7$ is 1H-imidazol-1-yl or morpholino and $R_8$ is alkyl($C_1$-$C_3$), phenyl or monosubstituted phenyl wherein the substituents are alkyl($C_1$-$C_3$), halogen or trifluoromethyl; $R_3$ is 2-pyridinyl, 3-pyridinyl, 2-methyl-3-pyridinyl, 4-methyl-3-pyridinyl, 2-furanyl, 5-methyl-2-furanyl, 2,5-dimethyl-3-furanyl, 2-thienyl, 3-thienyl, 5-methyl-2-thienyl, 2-phenothiazinyl, 4-pyrazinyl, 2-benzofuranyl, 2-(pyridine-N-oxide), 3-(pyridine-N-oxide), 4-(pyridine-N-oxide), 1H-indol-2-yl, 1H-indol-3-yl, 1-methyl-1H-pyrrol-2-yl, 4-quinolinyl, 4-pyridinyl methyl iodide, dimethylaminophenyl or N-acteyl-N-methylaminophenyl; $R_4$ is hydrogen or alkyl($C_1$-$C_3$); and $R_5$ is hydrogen or alkyl($C_1$-$C_3$); and the pharmacologically acceptable acid-addition salts thereof.

* * * * *